US010729358B2

(12) United States Patent
Ryan et al.

(10) Patent No.: US 10,729,358 B2
(45) Date of Patent: Aug. 4, 2020

(54) MEDICAL DEVICES AND RELATED METHODS

(71) Applicant: Aseptika Ltd, Cambridgeshire (GB)

(72) Inventors: Paul Thomas Ryan, Cambridgeshire (GB); Kevin Andrew Auton, Cambridgeshire (GB)

(73) Assignee: Aseptika Ltd, Cambridgeshire (GB)

( * ) Notice: Subject to any disclaimer, the term of this patent is extended or adjusted under 35 U.S.C. 154(b) by 249 days.

(21) Appl. No.: 15/514,437

(22) PCT Filed: Sep. 21, 2015

(86) PCT No.: PCT/GB2015/052712
§ 371 (c)(1),
(2) Date: Mar. 24, 2017

(87) PCT Pub. No.: WO2016/046522
PCT Pub. Date: Mar. 31, 2016

(65) Prior Publication Data
US 2017/0296104 A1    Oct. 19, 2017

(30) Foreign Application Priority Data

Sep. 25, 2014  (GB) .................................. 1416899.1
Sep. 25, 2014  (GB) .................................. 1416900.7

(51) Int. Cl.
*A61B 5/11*  (2006.01)
*A61B 5/00*  (2006.01)
(Continued)

(52) U.S. Cl.
CPC .......... *A61B 5/1118* (2013.01); *A61B 5/1455* (2013.01); *A61B 5/14551* (2013.01);
(Continued)

(58) Field of Classification Search
CPC . A61B 5/1118; A61B 5/14551; A61B 5/7275; A61B 5/681; A61B 5/1455; A61B 5/6826; G16H 50/30
(Continued)

(56) References Cited

U.S. PATENT DOCUMENTS 3,998,550 A    12/1976  Konishi et al.
4,167,331 A     9/1979  Nielsen
(Continued)

FOREIGN PATENT DOCUMENTS

EP    0 968 681 A1    1/2000
EP    2 022 394 A1    2/2009
(Continued)

OTHER PUBLICATIONS

International Search Report and Written Opinion dated Feb. 22, 2016 in connection with International Application No. PCT/GB2015/052712.
(Continued)

*Primary Examiner* — Nathan J Jenness
(74) *Attorney, Agent, or Firm* — Wolf, Greenfield & Sacks, P.C.

(57) ABSTRACT

We describe a user exercise-tolerance measuring pulse oximeter system, for determining the exercise tolerance or capacity of a user undergoing exercise, the system comprising: a wireless fingerband comprising an optical sensor to provide an oxygen saturation signal, a chargeable power supply, and a wireless transmitter/receiver; a motion detector to provide a user motion signal; and a signal processor coupled to said wireless fingerband to data from said optical sensor, and coupled to said motion detector; wherein said signal processor is configured to: process a combination of said oxygen saturation signal and said user motion signal to determine exercise tolerance data, wherein said exercise
(Continued)

tolerance data is dependent upon said oxygen saturation signal and a level of exertion of said user determined from said user motion signal; and to time or count a period or quantity of user motion or movements, during said exercise, identified by said motion detector, to determine said level of exertion; to measure a degree of oxygen desaturation of blood of said user due to said exercise; and to output an exercise tolerance parameter; wherein said exercise tolerance data comprises said exercise tolerance parameter; and wherein said exercise tolerance parameter is a function of both said degree of desaturation and said level of exertion.

8 Claims, 9 Drawing Sheets

(51) Int. Cl.
    *A61B 5/1455*    (2006.01)
    *G16H 20/30*    (2018.01)
    *G16H 50/30*    (2018.01)
    *G16H 40/63*    (2018.01)

(52) U.S. Cl.
    CPC ............ *A61B 5/681* (2013.01); *A61B 5/6826* (2013.01); *A61B 5/7275* (2013.01); *G16H 20/30* (2018.01); *G16H 50/30* (2018.01); *G16H 40/63* (2018.01)

(58) Field of Classification Search
    USPC ................................ 600/300, 301, 323, 324
    See application file for complete search history.

(56) References Cited

U.S. PATENT DOCUMENTS

| | | | |
|---|---|---|---|
| 4,407,290 A | | 10/1983 | Wilber |
| 4,773,422 A | | 9/1988 | Isaacson et al. |
| 5,413,100 A | * | 5/1995 | Barthelemy ....... A61B 5/14551 600/326 |
| 5,964,701 A | * | 10/1999 | Asada ................ A61B 5/02438 600/300 |
| 6,402,690 B1 | * | 6/2002 | Rhee .................... A61B 5/0002 600/300 |
| 2003/0073884 A1 | | 4/2003 | Goldberg |
| 2006/0217603 A1 | | 9/2006 | Nagai et al. |
| 2007/0038050 A1 | | 2/2007 | Sarussi |
| 2007/0106132 A1 | * | 5/2007 | Elhag .................. A61B 5/0205 600/301 |
| 2008/0015424 A1 | | 1/2008 | Bernreuter |
| 2008/0243393 A1 | | 10/2008 | Yamamoto et al. |
| 2008/0319327 A1 | | 12/2008 | Banet |
| 2009/0247837 A1 | * | 10/2009 | Ochs ................. A61B 5/14551 600/301 |
| 2010/0125188 A1 | | 5/2010 | Schilling et al. |
| 2010/0324384 A1 | * | 12/2010 | Moon ..................... A61B 5/746 600/323 |
| 2011/0040197 A1 | | 2/2011 | Welch et al. |
| 2011/0224498 A1 | | 9/2011 | Banet et al. |
| 2012/0130203 A1 | * | 5/2012 | Stergiou ............... A61B 5/0002 600/301 |
| 2014/0200420 A1 | | 7/2014 | Al-Ali |
| 2015/0208968 A1 | * | 7/2015 | Ennett .................. A61B 5/0022 600/323 |

FOREIGN PATENT DOCUMENTS

| | | | | |
|---|---|---|---|---|
| EP | 2 458 544 A1 | | 5/2012 | |
| JP | 2005-253865 A | | 9/2005 | |
| JP | 2009-066269 | * | 4/2009 | ............... A61B 5/14 |
| WO | WO 2010/103390 A1 | | 9/2010 | |
| WO | WO 2012/140559 A1 | | 10/2012 | |

OTHER PUBLICATIONS

International Preliminary Report on Patentability dated Aug. 30, 2016 in connection with International Application No. PCT/GB2015/052712.

Chung et al., A Wireless Sensor Network Compatible Wearable U-Healthcare Monitoring System Using Integrated ECG, Accelerometer and SpO2. Conf Proc IEEE Eng Med Biol Soc. 2008; 2008: 1529-32.

Fiore et al., Should oxyhaemoglobin saturation be monitored continuously during the 6-minute walk test? Chronic Respiratory Disease. 2011; 8(3):181-184.

Lee et al., Measurement of Motion Activity during Ambulatory Using Pulse Oximeter and Triaxial Accelerometer. Third 2008 International Conference on Convergence and Hybrid Information Technology. 2008; 1:436-441.

Pimenta et al., Desaturation-distance ratio: a new concept for a functional assessment of interstitial lung disease. Clinics. 2010; 65(9):841-846.

* cited by examiner

MEDICAL DEVICES AND RELATED METHODS

CROSS-REFERENCE TO RELATED APPLICATIONS

This application is a National Stage Entry of PCT Patent Application No. PCT/GB2015/052712, filed Sep. 21, 2015 and entitled "MEDICAL DEVICES AND RELATED METHODS," which claims priority to Great Britain Patent Application No. 1416899.1, filed Sep. 25, 2014; and Great Britain Patent Application No. 1416900.7, filed Sep. 25, 2014. The foregoing applications are incorporated herein by reference in their entireties.

THE FIELD OF THE INVENTION

This invention generally relates to devices, methods and computer program code for monitoring health, in particular using pulse oximetry, and also to related pulse oximeter systems.

BACKGROUND TO THE INVENTION

There is a general need to improve techniques for monitoring, and stratifying by risk, various chronic respiratory conditions such as chronic obstructive pulmonary disease (COPD), cystic fibrosis, non-cystic fibrosis bronchiectasis, and asthma as well as other conditions.

One approach to assessing the severity of respiratory conditions is to use a standardised clinical exercise test. Exercise capacity is a strong predictor for the risk of morbidity due to respiratory disease and can be used in Secondary care, Primary care and Social care settings to assess a patient. Often, however, it requires specialised testing facilities. There are several ways to determine Exercise Capacity and this typically is achieved by inducing a state of oxygen desaturation in the subject whilst they undergo some form of physical activity.

The most popular clinical exercise tests in order of increasing complexity are stair climbing, a 6 minute walk test (6MWT), a shuttle-walk test, detection of exercise-induced asthma, a cardiac stress test (e.g. Bruce protocol), and a cardiopulmonary exercise test. Assessment of exercise capacity has traditionally been done by asking patients subjective recollections about their capabilities. However, patients vary in their recollection and may over or underestimate of their true functional capacity.

The 6MWT test measures the distance that a patient can quickly walk on a flat, hard surface in a period of 6 minutes. It evaluates the global and integrated responses of all the patient's physiological systems involved during exercise, including the pulmonary and cardiovascular systems, systemic circulation, peripheral circulation, blood, neuromuscular units and muscle metabolism.

However, it does not provide specific information on the function of each of the different organs and systems involved in exercise or the mechanism of exercise limitation, as is possible with maximal cardiopulmonary exercise testing: The self-paced 6MWT assesses the submaximal level of functional capacity. Most patients do not achieve maximal exercise capacity during the 6MWT; instead, they choose their own intensity of exercise and are allowed to stop and rest during the test and this can affect the biometric parameters such as $SpO_2$.

To compensate for this, some advocate that tests should have a fixed level of load (e.g. the Shuttle Test or the TChester). However, because most activities of daily living are performed at submaximal levels of exertion, the 6MWT may better reflect the functional exercise level for daily physical activities. The 6MWT is used as a one-time measure of functional status of patients, as well as a predictor of morbidity and mortality.

Formal cardiopulmonary exercise testing provides an overall assessment of the exercise response, an objective measurement of functional capacity and impairment, determination of the appropriate intensity needed to perform prolonged exercise, quantification of factors limiting exercise, and a definition of the underlying pathophysiologic mechanisms such as the contribution of different organ systems involved in exercise. But this requires a laboratory setting and skilled staff to perform the test.

Further, 6MWT does not determine peak oxygen uptake, diagnose the cause of dyspnea (breathlessness) on exertion, or evaluate the causes or mechanisms of exercise limitation but information provided by a 6MWT is generally considered to be complementary to cardiopulmonary exercise testing, not a replacement for it.

Despite the difference between these Exercise Capacity tests, there are good correlations between these and with disease prognosis. For example, there is good agreement between the 6MWT and peak oxygen uptake for patients with end-stage lung diseases. In some clinical situations, the 6MWT provides information that may be a better index of the patient's ability to perform daily activities than peak oxygen uptake; for example, 6MWD correlates better with indices for the quality of life and changes in 6MWT after therapeutic interventions correlate with subjective improvement in dyspnea.

In another approach, the shuttle-walking test is used which is similar to the 6MWT, but it uses an audio signal from a tape cassette to direct the walking pace of the patient back and forth on a 10 m course. The walking speed is increased every minute and the test ends when the patient cannot reach the turnaround point within the required time. The exercise performed is similar to a symptom limited, maximal, incremental treadmill test. An advantage of the shuttle walking test is that it has a better correlation with peak oxygen uptake than the 6MWT. Disadvantages include less validation, less widespread use, and more potential for cardiovascular failure while it is being performed.

The 6MWT should preferably be performed indoors, along a long, flat, straight, enclosed corridor with a hard surface. However finding a suitable location for a patient to undertake this in the home environment can be challenging. Before and after the 6MWT, the technician will typically measure several parameters, including the distance walked within 6 minutes at the patient's own pace (the 6MWD distance) and the levels of oxygenation of the patient's blood ($SpO_2$) before and after (measuring the degree of desaturation). In practice, $SpO_2$ is not used for constant monitoring during the exercise because of the known issues of movement artefacts and difficulties in interpreting the results, but this has been recommended ("Should oxyhaemoglobin saturation be monitored continuously during the 6-minute walk test?", Fiore et al. (2011). Chronic Respiratory Disease. Vol 8. No. 3 181-184). While now well established and researched, the 6MWT requires facilities and skilled technicians to perform it. Nonetheless poor Q&A, different technicians, and inconsistencies create data of poor and unreliable quality.

More recently, Researchers have proposed an exercise capacity analysis in the form of a simple Sit-to-Stand (STS) test, as a way of inducing exercise-related deoygenation in patients with severe respiratory disease and this can be used in assessing progressive decline of lung function and providing a simple way to make a prognosis for the patient.

The test is simple: Count how many times a patient can move from the sitting position to the standing position and back down again in one minute. The theory and observation is that as lung function declines, the number of repetitions that a patient can undertake reduces. Every reduction in repetition count was associated with increased risk. Performance in the test is strongly associated with health and quality of life but not a predictor of exacerbation or flare-up of recurrent chest infections associated with long-term respiratory disease. Exercise capacity during the STS test is strongly associated with mortality—for example in one study the STS test was shown to be a stronger predictor of 2-year mortality than body mass index and an inability to undertake 19 reps or less held a high chance of mortality within 24 months.

Whatever the method used to induce oxygen desaturation during exercise, using just the distance walked or number of reps undertaken is still highly variable and these tests have to be performed carefully so that the patient invests the same level of effort on each test. This also makes it difficult to compare the level of risk between subjects.

There have been attempts to improve upon the data provided by such tests by measuring the degree of oxygen desaturation ($SpO_2$) induced by the exercise ("Desaturation-distance ratio: a new concept for a functional assessment of interstitial lung disease", Pimenta et al. (2010). Clinic Science 65(9):841-846). In practice, however, it is difficult for a user to perform a reliable test by themselves, at home.

Pulse Oximeters

Another difficulty which arises in this context is the difficulty of obtaining reliable oxygenation data from pulse oximetry. The signal detected by a pulse oximeter is small and easily affected by movement. Typically a finger clip is used to analyse pulsing arterial blood, but in practice such clips do not fit well. The measurement is very susceptible to errors resulting from, for example, selection of an inappropriately sized clip, poor clip placement, and any small motion by the patient which can disturb the position of the optical sensor arrangement within the clip with respect to the finger. Various attempts have been made to address this latter problem by incorporating an accelerometer in the pulse oximeter to detect patient motion so that data is only captured when the patient is stationary and is disregarded when the patient is moving. Such approaches are described in: US2010/0324384, US2010/0125188, and WO2010/103390.

For example, US2010/0324384, describes a wrist-worn transceiver incorporating an accelerometer with a wired connection to a plastic clip fastened with a strap to the base of a user's thumb, the clip comprising the sensor (LEDs and photodetector), the wrist-worn unit amplifying, filtering, digitising and processing the sensor signals to measure SpO2. However neither inherent resistance to movement, nor long-term use are considered.

Pulse oximetry measures blood oxygen (as oxyhaemoglobin) and relies upon the measurement of optical absorbance, at two or more wavelengths, of perfused tissue. Typically arterial oxygenation is distinguished from venous and other effects by sensing the varying portion of optical absorbance. This means, however, that the measurement tends to be very sensitive to movement. The problem is that the varying portion is typically a very small part of the overall absorbance (around 1%, but often significantly less). Small movements of the tissue and/or the sensor inevitably cause apparent changes in absorbance, often much larger than this level. Much development has been directed at solving this problem, both by design of the sensor and processing of the signals from the sensor.

Sensing is typically done by using a pair of light emitting diodes (LEDs) as sources of light—at wavelengths that show different absorbance for oxygenated and deoxygenated haemoglobin e.g. 660 nm and 940 nm, as is well known. The LEDs are positioned at one side of a section of perfused tissue and a single silicon diode photosensor is positioned on the opposite side to receive light passed through the section. This is "transmission" mode; an alternative is to place the emitters and sensor on the same side of the tissue—"reflection" mode, where diffuse reflection within the tissue allows measurement of optical absorbance to some depth within the tissue.

Various locations on the body are known as preferred locations for sensors for pulse oximetry. Most commonly fingertips are used because they are readily accessible, are well supplied with arterial flow and are of an appropriate thickness. Further, the anatomy is relatively simple and consistent between individuals. It is, however, somewhat inconvenient for subjects, particularly when bulky and/or heavy sensors are used. The wrist would be a more convenient location for subjects but it is much less suitable for pulse oximetry because the anatomy is very complex and the exact location of a sensor in relation to bones and tendons becomes a problem; small movements cause large changes in sensed signals. The large overall thickness of the wrist also means that very little light passes through, therefore needing more power to generate stronger illumination and making signal recovery much more difficult and unreliable. Other locations that are used include:

"Base" of the finger—weaker pulsatile signal compared to the fingertip and not much more convenient for the subject Forehead—good for measuring brain oxygen but unacceptable for continuous monitoring in daily life Ear lobe—small pulsatile signal and sensitive to compression that excludes arterial flow Foot—good for infants in hospital but inconvenient and subject to much movement for continuous monitoring The fingertip, therefore, is the preferred location but improvements are desired. In particular:

Resistance of the sensing system to movement

Improve comfort and convenience for long-term monitoring.

As previously mentioned, particularly in pulse oximeter systems for determining the exercise tolerance or capacity of a user, it is desirable to reduce the sensitivity of the pulse oximeter to user movement.

General

Background prior art can be found in: US2008/243393; US2003/073884; US2011/040197; US2011/224498; US2008/319327; U.S. Pat. Nos. 3,998,550; 4,167,331; 4,407,290; 4,773,422; US2008015424; US2007/0038050; WO2012/140559; US2014/0200420; EP0968681A; US2010/210924; U.S. Pat. Nos. 5,795,052; 5,800,349; "Measurement of Motion Activity during Ambulatory Using Pulse Oximeter and Triaxial Accelerometer" Young-Dong et al. Convergence and Hybrid Information Technology, 2008. ICCIT '08. Third International Conference on (Volume: 1); and "A wireless sensor network compatible wearable u-healthcare monitoring system using integrated ECG, accelerometer and SpO2", Chung et al. Conf Proc IEEE Eng Med Biol Soc. 2008; 2008: 1529-32. doi: 10.1109/IEMBS.2008.4649460.

However there is a need for techniques to improve upon the health monitoring approaches which have been employed hitherto, in particular those using pulse oximetry.

SUMMARY OF THE INVENTION

According to a first aspect of the invention there is therefore provided a user exercise-tolerance measuring pulse oximeter system, for determining the exercise tolerance or capacity of a user undergoing exercise, the system comprising: a wireless fingerband comprising an optical sensor to provide an oxygen saturation signal, a chargeable power supply, and a wireless transmitter/receiver; a motion detector to provide a user motion signal; and a signal processor coupled to said wireless fingerband to data from said optical sensor, and coupled to said motion detector; wherein said signal processor is configured to: process a combination of said oxygen saturation signal and said user motion signal to determine exercise tolerance data, wherein said exercise tolerance data is dependent upon said oxygen saturation signal and a level of exertion of said user determined from said user motion signal; and to time or count a period or quantity of user motion or movements, during said exercise, identified by said motion detector, to determine said level of exertion; to measure a degree of oxygen desaturation of blood of said user due to said exercise; and to output an exercise tolerance parameter; wherein said exercise tolerance data comprises said exercise tolerance parameter; and wherein said exercise tolerance parameter is a function of both said degree of desaturation and said level of exertion.

In embodiments a motion detector such as an accelerometer is used to determine a level of exertion of the user/patient. This information is combined with a measure of oxygen saturation of the patient from an optical sensor of the pulse oximeter system so that the combination provides exercise tolerance data. More particularly the exercise tolerance data comprises (and may consist of) an exercise tolerance parameter which accurately measures the user's exercise capacity/tolerance. We later refer to such a parameter as a Respiratory Exercise Tolerance index (RET index). Preferably peripheral capillary oxygen saturation ($SpO_2$) is measured to measure the degree of oxygen desaturation during the exercise. It is difficult to get good oxygen saturation data from a user undergoing exercise but the inventors have found that by mounting the pulse oximeter optical sensor in a lightweight, close-fitting elastic fingerband with a wireless data connection and rechargeable power source to avoid a wired connection, movement artefacts can be substantially reduced. (The skilled person will appreciate that in this context reference to a "finger" include a thumb). Embodiments of the system thus enable a significantly more accurate measure of the relationship between oxygen desaturation and exertion, and also help to overcome difficulties such as imperfect compliance with a clinical exercise test.

Optionally embodiments of the system and later described method may be configured to administer one or more predetermined clinical exercises, for example a clinical exercise defined by internally stored or downloaded exercise definition data. In such embodiments the system may prompt the user to complete a particular exercise and/or notify the user if the exercise is not being correctly performed. For example the system/method may prompt the user to continue walking for a predetermined interval, for example to administer a walk test (VVT) such as a 6MWT and/or may prompt a user to adequately perform or continue a sit-to-stand (STS) test.

The invention also contemplates a system/method which monitors/prompts the user in such a manner without necessarily processing a combination of the oxygen saturation signal and user motion signal to determine the exercise tolerance data—where compliance with a particular exercise is monitored and ensured by the system/method it may not be necessary to employ the user motion signal to determine a level of exertion by the user; instead this may be determined from a known (for example stored and/or downloaded) value dependent upon the individual exercise. As noted below, this may be adapted according to characteristics of the user. In embodiments of the system/method in which a user is monitored/prompted to perform exercise, advantageously the system may include a user safety monitoring system, for example implemented as a computer programme code module, to detect when the safety of the user is at risk. This may be based, for example, on the oxygen saturation signal, or on some other signal such as a signal from a sensor monitoring the user's heart (or on a measured heart rate derived from the oxygen saturation signal), so that the test can be halted if there is potential danger to the user.

In some preferred embodiments of the system a user data input device is provided to receive data characterising the individual user. This may be, for example, in the form of a user interface on the pulse oximeter and/or an associated fixed or mobile computing device. Such data may comprise, for example, user weight, user height, user body mass index, a measure of user body fat (for example from a skinfold test), user age, and/or user gender. This information may be employed to more accurately determine the level of exertion of the user, for example by determining a level of energy expenditure of the user during the period of exercise. The level of energy expenditure may be estimated dependent, for example, on one or more of: an amplitude of measured motion, a duration of measured motion, an integrated accelerometer or motion signal; and optionally further including a component dependent on one or more body characteristics such as height, weight, metabolic rate and the like. Capturing a user weight and/or body mass index value is particularly useful in this respect.

Additionally or alternatively the user characterising data may be employed to compensate one or more of the oxygen saturation/desaturation data, the level of exertion, and the exercise tolerance data to provide some compensation for volumetric lung capacity—user height is particularly advantageous as a surrogate in this respect.

More generally it is known that oxygen consumption during exercise depends upon age, and potentially gender ("Accelerometer derived activity counts and oxygen consumption between young and older individuals", Whitcher L and Papadopoulos C., Journal of Aging Research, Hindawi Publishing Corp., Volume 2014, Article ID 184693, hppt://dx.doi.org/10.1155/2014/184693). In embodiments the level of exertion and/or oxygen saturation and/or exercise tolerance data may be adjusted dependent on the user characterising data. For example a look up table may be employed; this may be a one- or multi-dimensional table defining one or more ranges of the user characterising data values: the user characterising data may be employed as an index to the table to determine an adjustment or compensation to be applied. In other approaches a mathematical function or formula may be employed.

A similar approach may be employed when determining the exercise tolerance data or parameter from the oxygen (de)saturation and user exertion. Thus in one approach a simple mathematical relationship or function may be employed to combine the oxygen saturation data and level of exertion. For example a simple ratio of desaturation to exertion may be determined to determine an exercise tolerance parameter. However the relationship between exercise tolerance and exertion is not necessarily linear and a more sophisticated approach may be employed in which, for example, a treadmill based experiment may be employed to determine calibration data. This may then be encoded in the system, for example as a look up table or in some other way (for example using machine learning) to encode a relationship between determined level of exertion, oxygen saturation measurements, and exercise tolerance.

Such an approach may in principle be extended so that in embodiments of the system rather than determining a level of exertion as such the motion data is processed to determine a signal representing a level of exertion (for example) a simple peak-to-peak amplitude of motion). Data of this type may then be processed directly or indirectly in combination with the oxygen (de)saturation signal to determine the exercise tolerance data, more particularly an exercise tolerance parameter, without necessarily determining an absolute measure of energy expenditure, for example in the form of calories burned.

In embodiments of the invention described later, which employ continuous monitoring of oxygen saturation and/or an integral or time derivative of this value, similar approaches may be employed to processing the measured/derived data. Optionally this may be combined with administering one or more standard tests (which may be empirically determined). Exercise tests conducted in clinical settings have demonstrated that the results of these tests are a strong predictor of two-year mortality—for example the inability to perform a threshold number of repetitions of the STS test can indicate a greater than evens chance of mortality within twenty four months. In embodiments of the invention the system/method provides an exercise tolerance parameter as an output which is a predictor of the risk of mortality within twenty four months.

In some embodiments the system combines the data on the level of exertion by the user with a measure of the user's blood oxygen saturation/desaturation immediately before and after the period of exercise. Because oxygen desaturation following exercise recovers relatively quickly it is advantageous to use the motion detector to detect the cessation of exercise, and responsive to that to measure the level of oxygen (de)saturation, so that the level is measured substantially immediately after the exercise. Nonetheless in embodiments of the system the level of oxygen saturation of the user's blood may also be monitored during the exercise, either substantially continuously or at intervals. This latter approach is advantageous in that additional useful data is provided relating to the exercise capacity/tolerance of the patient. More particularly the oxygen desaturation represents a deficit between the body's ability to take in oxygen from the air and the body's use of oxygen.

Thus in broad terms the cumulative value or integral of a parameter representing the (de)oxygen saturation in the user is related to an oxygen debt of the user accumulated over the period of the exercise. This information may be incorporated into a single exercise tolerance parameter and/or may be provided either explicitly or implicitly as part of a set of exercise tolerance data provided by the system. In embodiments the integral may be an integral of the difference between 100% saturation and the measured level of oxygen saturation, that is an integral of the effective oxygen desaturation of the user. Optionally the exercise tolerance parameter may be determined based solely upon this integral value. More generally a cumulative value comprising a combination of one or more of an integral, a final desaturation, and a derivative may be employed.

In a similar manner the system may determine a continuous or discreet time derivative of the user's oxygen saturation. In broad terms this represents the rate of fall of oxygenation of the user's blood during exercise, and again may be employed to provide additional exercise tolerance data and/or as the sole measure of exercise tolerance. Further optionally where, as described above, a safety system is incorporated an alert or exercise cessation signal may be generated dependent on the determined rate of drop of oxygen saturation being greater than a threshold value.

As previously mentioned, it is relatively difficult to get good oxygen saturation data from a user in motion. One approach to obtaining this data is to employ signal processing to monitor the plethysmographic data from the pulse oximeter to identify locations in the trace where the data is stable, selectively measuring oxygen saturation from the measurements made during these intervals. Regions of stable data may be identified in many ways including, for example, using adaptive classification techniques. However, as previously described, embodiments of the system employ a pulse oximeter optical sensor arrangement mounted in a close-fitting elastic fingerband, which substantially reducing movement artefacts (although additional signal processing may also be employed).

In embodiments the fingerband is a wireless device incorporating a chargeable power supply and a wireless transmitter/receiver, for sending a signal from the optical sensor arrangement to the signal processor and for receiving radio frequency power to charge the chargeable power supply and/or data or a control signal(s). Use of wireless technology facilitates obtaining a good quality signal from the sensor because of the significant reduction in movement artefacts caused by the wired connection of a wired sensor. The data/signal(s) which may be sent from a processor, say in a wrist unit, to the fingerband sensor may include, for example, data defining when a measurement is or is not to be made, movement data (optionally comprising rate of movement data), heart rate data or heart beat timing data, and control data such as a request for data to be downloaded from local storage on the fingerband. The skilled person will appreciate that such control arrangements may also be applied to a remote sensor/processor unit configured to be located on a body part other than a finger or thumb, such as the forehead or earlobe.

The skilled person will appreciate that the signal processor may comprise one or more processors in, for example, a wrist unit or the signal processor may be a distributed signal processor, distributed across multiple devices. For example the signal processor may be implemented across a wrist-mounted unit and a smart phone to which the wrist unit may be coupled.

In some preferred embodiments the signal processor is incorporated in a wrist-mounting unit linked to the fingerband-mounted optical sensor, preferably wirelessly. In such an arrangement the motion sensor (accelerometer) may be incorporated into the wrist-mounting unit; preferably this unit also provides a user interface and wired, or preferably wireless, communications to a network such as a computer network. In other approaches, however, the motion detector (accelerometer) may be provided in a separate device such as a smartphone. In some preferred embodiments the signal processing is performed within the wrist-mounting unit but in other approaches the data from the optical sensor and/or motion detector may be provided to a remote server for processing elsewhere. Such a server may be located in a fixed or mobile computer of the user or elsewhere, for example in the cloud. In principal separate devices on the user may provide separate oxygen saturation and motion signals to a common remote data processing system where the data is processed and combined to determine the exercise tolerance data. In some preferred embodiments, however, the device is operable as a self-contained system comprising the wrist-mounting unit including the signal processor and the wireless fingerband, albeit in preferred embodiments the wrist mounting unit is provided with wireless communications to enable Internet access.

According to a further aspect of the invention there is provided a user exercise-tolerance measuring pulse oximeter system, for determining the exercise tolerance or capacity of a user undergoing exercise, the system comprising: an optical sensor to provide an oxygen saturation signal; a motion detector to provide a user motion signal; and a signal processor coupled to said optical sensor and to said motion detector; wherein said signal processor is configured to process a combination of said oxygen saturation signal and said user motion signal to determine exercise tolerance data, wherein said exercise tolerance data is dependent upon said oxygen saturation signal and a level of exertion of said user determined from said user motion signal.

In a related aspect the invention provides a method of determining exercise tolerance, the method comprising: using a motion detector to determine a level of exertion of a user during a period of exercise; using an optical sensor to determine a degree of oxygen desaturation of blood of said user during said period of exercise; combining said determined degree of oxygen desaturation and said determined level of exertion to determine an exercise tolerance parameter; and storing and/or outputting data dependent upon said exercise tolerance parameter.

As previously described, preferred embodiments including compensating for user characterising data such as user weight and the like. In embodiments the degree of oxygen saturation of the user's blood is measured concurrently during the period of exercise with the motion/level of exertion. Optionally the method may then further include determining an integral and/or time derivative of the oxygen saturation to determine the exercise tolerance parameter and/or additional user exercise tolerance data.

The skilled person will appreciate that embodiments of the above described system/method will generally be implemented using a signal processor, which may be a digital signal processor, or a microprocessor or microcontroller, or a personal computer or mobile computing device, under control of processor control code.

Thus the invention further provides processor control code to implement the above-described systems and methods. The code is provided on a non-transitory physical data carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code, or code for a hardware description language. As the skilled person will appreciate such code and/or data may be distributed between a plurality of coupled components in communication with one another.

In other aspects the invention provides a pulse oximeter comprising: fingertip-mounting optical sensor including a rechargeable power source; a wrist-mounting signal processor wirelessly coupled to said optical sensor; and a motion detector; wherein said pulse oximeter is configured to identify a level and/or duration of user motion and, responsive to said identification, determine and/or record blood oxygenation data; and/or wherein said pulse oximeter is configured to record, in tandem, motion data from said motion detector and blood oxygenation data from said optical sensor.

In embodiments the optical sensor includes a local signal processor to process a sensed optical signal; a chargeable power supply; and a wireless transceiver for sending a processed sensed optical signal to said wrist mounting signal processor, and for receiving RF power to charge said chargeable power supply.

In embodiments the pulse oximeter is configured to provide processed data, in particular an alert, dependent upon a combination of said motion data from said motion detector and said blood oxygenation data from said optical sensor.

The invention also provides a method of using a pulse oximeter as described above to determine and/or record blood oxygenation data, as the user performs physical activity, the method comprising: detecting said physical activity using said motion detector; and automatically determining and/or recording said blood oxygenation data before and after said physical activity in response to said detecting The invention further provides a method of using a pulse oximeter as described above comprising: determining and/or recording said blood oxygenation data during said physical activity; recording said motion data during said physical activity; and determining data representing a combination of said motion data from said motion detector and said blood oxygenation data from said optical sensor.

The skilled person will appreciate that these aspects of the invention may incorporate features from the previously described aspects and embodiments of the invention; and vice-versa.

We now describe further features and aspects of the invention which are particularly advantageous when used in combination with the above-described systems and methods but which may also be employed separately from the above-described systems and methods.

Pulse Oximeter Systems

According to a further aspect of the invention there is therefore provided a fingerband for a pulse oximeter system, the fingerband comprising: a pulse oximeter sensor; and a processing system coupled to said sensor, wherein said processing system comprises a processor coupled to non-volatile program memory and to working memory, said program memory storing processor control code to process a signal from said sensor and output processed data to a remote monitoring unit; and a rechargeable power supply coupled to said sensor and to said processing system to provide electrical power for said fingerband.

Broadly speaking, embodiments of the invention divide the signal processing between the fingerband and a remote unit, for example a wrist-mounting unit. This in turn facilitates, for example, local or remote control of measurements, local or remote heart beat synchronisation, wireless operation (thus reducing signal disruption by movement of a wired connection), long-term monitoring (for example by means of local, raw or processed, data storage), and other advantageous techniques. In a typical embodiment the pulse oximeter sensor comprises a pair of light sources operating at different wavelengths, typically red and infra-red, and at least one detector. The light sources illuminate the detector through a user's digit; multiple pairs of such sensors may be employed. For the avoidance of doubt, references herein to a 'fingerband' are to a band which fits around one of a user's digits, either finger or thumb (or potentially even, toe).

In embodiments the processing performed by the local signal processing system may comprise, for example, sampling one or more sensor signals; storing/retrieving sensor data; signal processing for example to identify a peak and/or trough of a waveform and/or to form signal averaging; and/or sample decimation. Some or all of these functions may be performed; typically some basic signal processing as performed in the analogue domain prior to digitisation, for example to extract an ac part of the sensor signal and/or to normalise the signal.

In some preferred embodiments, as described later, the fingerband electronics are embedded in an elastic material (elastomer). In embodiments the rechargeable power supply comprises a laminar or curved rechargeable battery.

In some preferred embodiments the processing system is able to operate autonomously to capture and process pulse oximetry data from the sensor and to communicate the processed data to the remote monitoring unit. Examples of various modes of autonomous operation are described later. In some preferred embodiments the processor control code includes code to process the raw signal data to provide a reduced data rate output, thus facilitating reduced power consumption/increased wireless range (with a wireless device). Thus in embodiments the fingerband processor determines a magnitude of pulsation of an oxygenation wave sensed by the sensor, for example a peak/trough difference, preferably with noise-reduction. In embodiments this includes tracking a heartbeat/rate of the user; this may be performed locally or at the remote monitoring unit, or in a manner which is distributed between both devices.

In some preferred embodiments the fingerband processing system further comprises data memory (optionally non-volatile; and which may be the same as the program memory), in particular so that data may be provided to the remote monitoring unit as a batch. This can be useful for example for power saving; where the remote monitoring unit is not necessarily carried by the user; and potentially where batch download of data is performed when the fingerband is remotely powered, by either a wired or wireless connection (for example an intermittent download, when powered, capability).

In embodiments the signal processing system is configured to adapt a rate of data capture from the sensor dependent on a measure of quality of the sensor signal/captured data. Counter-intuitively, where a low quality of captured data is detected, rather than retry immediately the system may delay a further measurement, for example by a defined duration. This is predicated on the assumption that poor signal quality is caused by motion, giving the user time to cease the motion.

In some preferred embodiments the fingerband electronics includes a wireless communications module for wireless communication with the remote monitoring unit. This may simply transmit data to the remote monitoring unit, but in preferred embodiments the wireless link is bi-directional, to facilitate measurement trigger and/or mode control and the like. Preferably the wireless link is a radio frequency link. Employing a wireless communications link helps to make the fingerband more robust to movement, especially if the fingerband is small and light. With a wireless system the above-described processing techniques are particularly advantageous in achieving improved battery life/rf range.

A wireless fingerband may incorporate a wired or wireless charging system for the rechargeable power supply. For example the fingerband may incorporate a power supply connection such as a pair of contacts, for example gold contacts. A wireless charging system may comprise a coil, preferably wound circumferentially around the fingerband to facilitate coupling to a charger, for example by placing the fingerband over a magnetic core of an inductive charging device. With such an arrangement, however, the coil can inhibit stretching of the fingerband so that is can be placed over a user's digit. Thus in some preferred embodiments the fingerband electronics, more particularly a circumferential portion of wire or coil, incorporates a meander such as a V'-shaped insert, loop or other length-extending feature, so that the fingerband may still be stretched and readily fitted by a user.

In a related aspect, therefore, the invention provides a fingerband comprising fingerband electronics indicating at least a pulse oximeter sensor, wherein said fingerband comprises an elastomer in which said fingerband electronics are substantially embedded.

As previously described, typically the pulse oximeter sensor comprises an electro-optic detector and at least one pair of electro-optic emitters. In preferred embodiments the fingerband electronics includes a communications system to communicate to/from a remote monitoring unit, and a local power supply such as a (curved) battery. In embodiments the fingerband electronics comprises a coil to provide communication to and/or from the remote unit and/or for receiving power to charge the battery. Preferred embodiments of the fingerband electronics comprise a digital controller (processor), but in principle analogue processing and communications may be employed.

Such a fingerband may incorporate one or more of the previously described features. In some preferred embodiments the fingerband elastomer incorporates an optical shield to shield the detector from ambient light of at least the two different wavelengths of the emitters. In embodiments the elastomer is relatively soft, for example in the range 20-40 Shore A. As previously described in preferred embodiments the fingerband electronics include one or more systems to enable the electronics to be stretched whilst the fingerband is fitted, for example incorporating one or more wires with a meander such as a 'V'-shaped insert, loop or other length-extending feature.

In some preferred embodiments the fingerband has an anti-perspiration layer on an inner surface (that is the surface which lies against the digit). This may comprise, for example, a layer of fibrous material and/or a set of axial grooves (that is generally parallel to a longitudinal axis of the fingerband).

In embodiments the fingerband may be configured to fit over the distal and intermediate phalanges of a user's digit, to either side of a joint, the fingerband preferably then incorporating one or more openings in the band in a region of the joint. This facilitates robustness to movement and long-term use with reduced interference to dexterity.

In a still further aspect the invention provides a pulse oximeter system comprising: a fingerband incorporating a pulse oximeter sensor coupled to a first processor; and a remote unit, coupleable to said fingerband, comprising a second processor; wherein signal processing of one or more signals from said sensor to determine a blood oxygenation measurement is shared between said first processor and said second processor.

The skilled person will appreciate that the processor may be a digital signal processor, or a microprocessor or microcontroller, under control of processor control code. The invention further provides processor control code for a fingerband/system as described above. The code is provided on a non-transitory physical data carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code, or code for a hardware description language. As the skilled person will appreciate such code and/or data may be distributed between a plurality of coupled components in communication with one another.

In embodiments the fingerband may be used with a pulse oximeter as described in our co-pending application, ibid. Thus a pulse oximeter system including the fingerband may further comprise a wrist-mounting signal processor wirelessly coupled to the fingerband and a motion detector. The pulse oximeter system may be configured to identify a level and/or duration of user motion and, responsive to said identification, determine and/or record blood oxygenation data. Additionally or alternatively the pulse oximeter system may be configured to record, in tandem, motion data from said motion detector and blood oxygenation data from said optical sensor. In embodiments the pulse oximeter system is configured to provide processed data, in particular an alert, dependent upon a combination of motion data from the motion detector and blood oxygenation data from the fingerband.

In the same or other embodiments the fingerband may be used in a user exercise-tolerance measuring pulse oximeter system, for determining the exercise tolerance or capacity of a user undergoing exercise, the system comprising: the fingerband, to provide an oxygen saturation signal; a motion detector to provide a user motion signal; and a signal processor coupled to the fingerband and to the motion detector; wherein said signal processor is configured to process a combination of the oxygen saturation signal and the user motion signal to determine exercise tolerance data or an exercise tolerance parameter, wherein the exercise tolerance data/parameter is dependent upon the oxygen saturation signal and a level of exertion of the user determined from the user motion signal, for example by timing or counting a period or quantity of user motion or movements. Preferably in such a system the processor is configured to receive user characterising data comprising one or more of: user weight, user height, user age, user gender, and user body mass index; and the signal processor is configured to determine the level of exertion dependent on the user characterising data.

BRIEF DESCRIPTION OF THE DRAWINGS

These other aspects of the invention will now be further described, by way of example only, with reference to the accompanying figures in which.

DETAILED DESCRIPTION OF PREFERRED EMBODIMENTS

Figure 1:
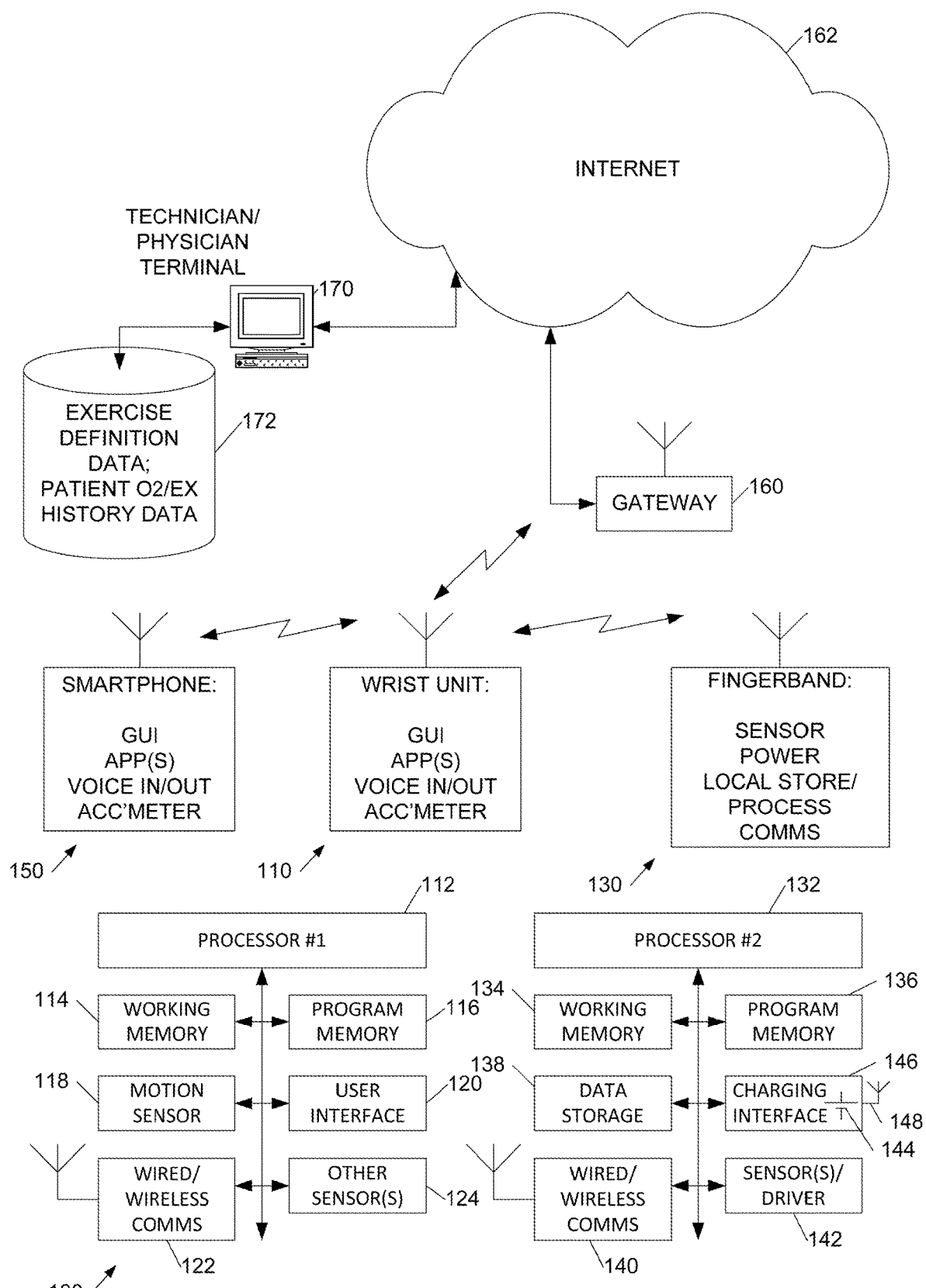
FIG. 1 shows a block diagram of a pulse oximeter system according to an embodiment of the invention.

Referring to FIG. 1, this shows a block diagram of a pulse oximeter system 100 according to an embodiment of the invention. The pulse oximeter system comprises a wrist unit 110, comprising a first signal processing system, wirelessly coupled to a fingerband 130, comprising a pulse oximeter optical sensor coupled to a second signal processing system. Optionally the wrist unit and/or fingerband may also be coupled to a smartphone, smartwatch, or other personal digital device 150. In embodiments the wrist unit is wirelessly coupled to one or more other devices by a short range wireless communications link such as a Bluetooth™ link, although a wired connection may in principal be employed. In some preferred embodiments the wrist unit 110 also includes a wireless interface to a gateway 160 to the internet 162; this may comprise a WiFi connection or a mobile phone connection (in which case the link may be via smartphone 150 or directly from the wrist unit).

As illustrated the system includes an optional technician/physician terminal 170, which may be employed to control wrist unit 110 and/or and send data to or retrieve data from the wrist unit. Thus in embodiments the terminal 170 is coupled to a database 172 which stores a patient (history) data, more particularly captured oxygen saturation data and associated data defining a level of patient exertion relating to the oxygen saturation data, and optionally other data, such as derived exercise tolerance or parameter data. Preferably such data is stored as a series of exercise episodes which may be interrogated, displayed graphically, analysed, and the like via terminal 170. Additionally or alternatively database 172 may store exercise definition data, that is data which may be provided to wrist unit 110 to define one or more exercises to be performed by the user/patient. Thus this data may comprise a definition of the exercise (walk test, sit-to-stand test and so forth) in conjunction with one or more exercise-defining parameters such as a duration of the exercise and/or number of repetitions and/or data defining a minimum degree or speed of motion required by the exercise. Optionally this may be stored in conjunction with data defining commands such as voice or visual commands for instructing the user/patient to begin/end a period of exercise.

The wrist unit 110 comprises a processor 112 coupled to working memory 114, and program memory 116, such as Flash memory, storing firmware for the wrist unit. The processor is also coupled to a motion sensor 118 such as an accelerometer and to a user interface 120, for example a touch-sensitive display or audio (voice input/output) interface; as well as to wired and/or wireless communications 122 and optionally to one or more additional sensors 124, for example a temperature sensor, ECG sensor and the like. Such other sensors may be integrated with the writs unit of may be provided separately. Optionally some or all of the functions of wrist unit 110 may be performed by a smartphone or smartwatch 150: typically all the functions of wrist unit 110 are present in a smartphone, including an accelerometer and a Bluetooth™ link, and appropriate software can be provided by an "app". Thus in embodiments the invention contemplates substituting a smartphone or smartwatch for the wrist unit.

In preferred embodiments the fingerband 130 mounts a pulse oximeter sensor system, as described further later, and includes a rechargeable power supply to enable the fingerband to operate independently of the wrist unit. In preferred embodiments the chargeable power supply comprises a laminar, curved battery such as a lithium-ion battery but other approaches, such as a super capacitor, may also be employed. Additionally preferred embodiments of the fingerband include local storage/processing for the data from the sensors, in particular to pre-process the sensor data to reduce the data rate from the fingerband to the wrist unit and/or to facilitate batch data transfer from the fingerband to the wrist unit.

Thus embodiments of the fingerband comprise a processor 132 coupled to working memory 134 and program memory 136 such as Flash storing firmware for the fingerband. The processor 132 may also be coupled to non-volatile data storage 138 (potentially combined with program memory 136), to a wired and/or wireless communications interface 140 such as a short range Bluetooth™ link, and to a set of sensors/drivers for a pulse oximeter sensor system 142. In embodiments the rechargeable power source 144, more particularly the curved battery, is provided with a charging interface 146 which may be arranged to receive wired or preferably wireless power via antenna 148 for recharging the battery. Optionally the charging system 146 may also interface to processor 132.

Figure 2:
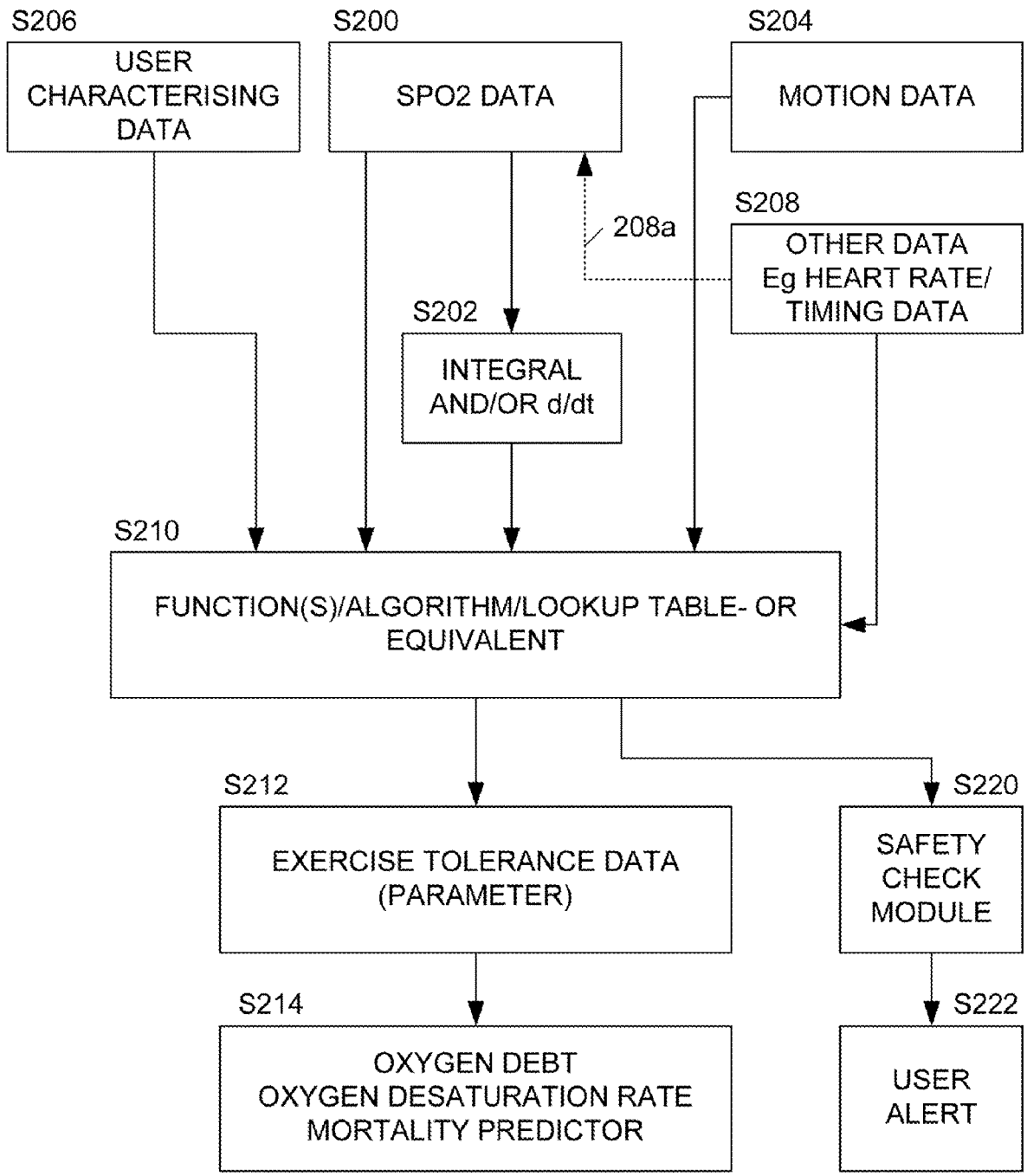
FIG. 2 shows a flow diagram illustrating operation of the system of FIG. 1.

Referring now to FIG. 2, this shows a flow diagram of processing performed by the wrist unit and/or smartphone of FIG. 1 (although as a skilled person will appreciate, in principal some or all of the processing could be performed in the cloud).

Thus at step S200 the system captures oxygen saturation data, preferably in the form of an $SpO_2$ level signal, before and after an episode of exercise, preferably a predefined physical exercise test. In some preferred embodiments this data is also collected at intervals or substantially continuously during the exercise, in which case additional processing (S202) may be applied, in particular to determine an integral and/or time derivative of the $SpO_2$ level data. The $SpO_2$ level data and optionally additionally derived data from step S202 provide one or more inputs to a procedure (S210) which derives data and/or one or more parameters from a combination of the oxygen saturation data and data determining a degree of exertion of the user.

Thus the procedure also receives user motion data (S204), which is preferably derived from the motion sensor 118 of FIG. 1. This motion data may comprise data from an accelerometer which may be used to determine a degree of motion of the user, as a proxy for a level of exertion of the user. Thus, for example, the accelerometer data may be employed to determine a distance travelled by the user during the exercise and/or a measure of speed of motion of the user during the exercise such as an average or maximum speed of motion. Additionally or alternatively the accelerometer data may be employed to determine an amplitude or magnitude (excursion) or count of a repetitive motion performed by the user, for example during a sit-to-stand test or during a walk test. This can provide another indication, in effect, of total distance moved by the user.

Whilst preferably the motion data is captured from the motion sensor, this is not essential and in principal a level of exertion of a user may be determined simply by timing a duration of an episode of exercise. This latter approach may involve prompting the user to start and stop the exercise; in this case optionally the motion sensor may be used to determine that the user is continuing to perform at greater than a minimum threshold level of exertion/motion during the period of the exercise. In this case the motion data is therefore used to monitor that the exercise is being performed adequately, and may potentially also be used to provide an indicator of data quality (compliance with the target exercise) and/or to prompt the user when a level of exercise is inadequate. Thus the motion data from step S204 provides a second input to the combined data processing step 210.

A third, optional, input to the combined data processing S210 is provided by user characterising data S206 such as user weight, height, BMI, age, gender and the like. This data may be input by a user, for example into wrist unit 110 or smartphone 150 or may already exist elsewhere, for example in database 172. An additional input (not shown) may define an exercise or exercise type, for example to provide a scaling value to processing S210 dependent on the exercise selected. The user characterising data can be used to adjust the input data, for example to scale and/or offset data derived from the motion data, to determine a more accurate level of exertion of the user. For example a user with a large weight, weight to height ratio or BMI may undergo relatively greater exertion for the same degree of physical movement, and thus the motion data, or data derived from the motion data may be scaled by one or more of these factors. In addition an older user will generally have employ a greater level of exertion for the same degree of physical movement than a younger user, and thus age (and similarly gender) may be used to scale and/or offset the data defining a degree of movement of the user. Additionally, or alternatively user characterising data may be applied to an output of the processing of step S210, for example to modify an exercise tolerance parameter or mortality predictor based on one or more elements within the user characterising data, for example user age.

Optionally further data may be taken into account by the processing, for example heart rate data (which may be derived from the $SpO_2$ data or independently, for example from an ECG measurement). Optionally data defining a timing of the heartbeats (however determined) may be employed in processing the captured oxygenation ($SpO_2$) data as indicated by dashed arrow 208a in FIG. 2. For example the $SpO_2$ data may be sampled with a timing based upon the heartbeat timing.

At step S210 the oxygen saturation data and user motion data are combined to output exercise tolerance data (S212) and/or an exercise tolerance parameter. The data may be combined in many different ways; any particular technique selected can be validated by, example, performing exercise tests under clinical conditions. Such empirical validation may be used, for example, to confirm that a particular method of combining data correlates with other measures which may be made under clinical conditions and/or such an approach may be employed to correlate the exercise tolerance data with previously conducted clinical studies.

In one approach the processing at S210 determines a level of exertion of the user by applying a mathematical function to the motion data. The motion data may be, for example, data measuring the total distance moved by the user or data measuring the total distance in one or more directions, for example horizontally and vertically (upwards). The mathematical function applied to the motion data may also incorporate one or more parameters of the user characterising data as one or more variables on which the function is dependent. Such a mathematical function may also incorporate the change in oxygen saturation from the start to the end of the exercise as another variable on which the function is dependent, so that an exercise tolerance parameter may be a combined function of the input data. Alternatively, separate functions may be defined for the change in oxygen saturation and to define the level of user exertion, and the separate functions may then be combined to determine a parameter representing an exercise tolerance of the user.

Where available integral and/or time derivative data may be included in one or more of these functions; or this integral or time derivative data may be the only oxygen saturation data employed by step S210. In embodiments the oxygen saturation data employed by the procedure comprises an oxygen desaturation level (and/or integral and/or derivative thereof). Thus a function employed by the processing step S210 may comprise a measure of desaturation of the user during the period of exercise. In one embodiment an integral (area under a curve) of the oxygen desaturation is determined and a function is defined comprising an inverse of this integral, in broad terms an inverse of the oxygen debt of the user accumulated during the exercise. With such an approach a high value indicates relatively greater tolerance to exercise. In embodiments this or any of the previously mentioned functions of oxygen (de)saturation is combined with data representing a level of exertion of the user by, for example, scaling and/or offsetting by the level of exertion. Thus in the previous example a parameter representing an (inverse) oxygen debt may be scaled by the level of exertion so that a high level indicating high exercise tolerance is increased further if the level of exertion during the exercise was also high.

In another approach "algorithmic" processing may additionally or alternatively be employed, for example to classify the oxygen (de)saturation data and/or motion/exertion data into one or more bands, determining exercise tolerance data and/or an exercise tolerance parameter based upon a corresponding classification of the captured user data.

In a still further approach, which may be combined with either of the preceding approaches, data from clinical tests may be employed to define a non-linear relationship between oxygen (de)saturation, movement/level of exertion, and exercise tolerance (the latter measured for example, by a physiologically validated approach). The skilled person will recognise that user characterising data may also be incorporated into such an approach. In broad terms this approach essentially comprises calibrating the system with measured input data (oxygenation; motion/exertion; user characteristics) and measured output data (for example physiologically determined exercise tolerance) and then embodying the (potentially non-linear) calibration in the processing step S210. This calibration may be embodied in the processing step in many ways including, for example, by means of one or more look-up tables (based on continuous valued or banded data inputs), or by machine learning techniques, for example a classifier or neural network, or in other ways. Optionally the processing step S210 may determine a measure of (or a proxy for) one or more of oxygen debt, from (de)saturation integration, and oxygen desaturation rate, from (de)saturation time derivative data. Additionally or alternatively a mortality predictor parameter may be determined, which may be the same as, or correspond to, the previously discussed exercise tolerance parameter, since there is a relationship between exercise tolerance and predicted mortality, for example two-year mortality.

In embodiments, in particular those in which a user is prompted by the system to begin/maintain exercise, the procedure may incorporate a safety check (S220). This may involve monitoring the level of oxygen (de)saturation and/or the user's heart rate and producing an audible and/or visual user alert (S222) if either or both these exceeds a predetermined threshold.

Figure 3:
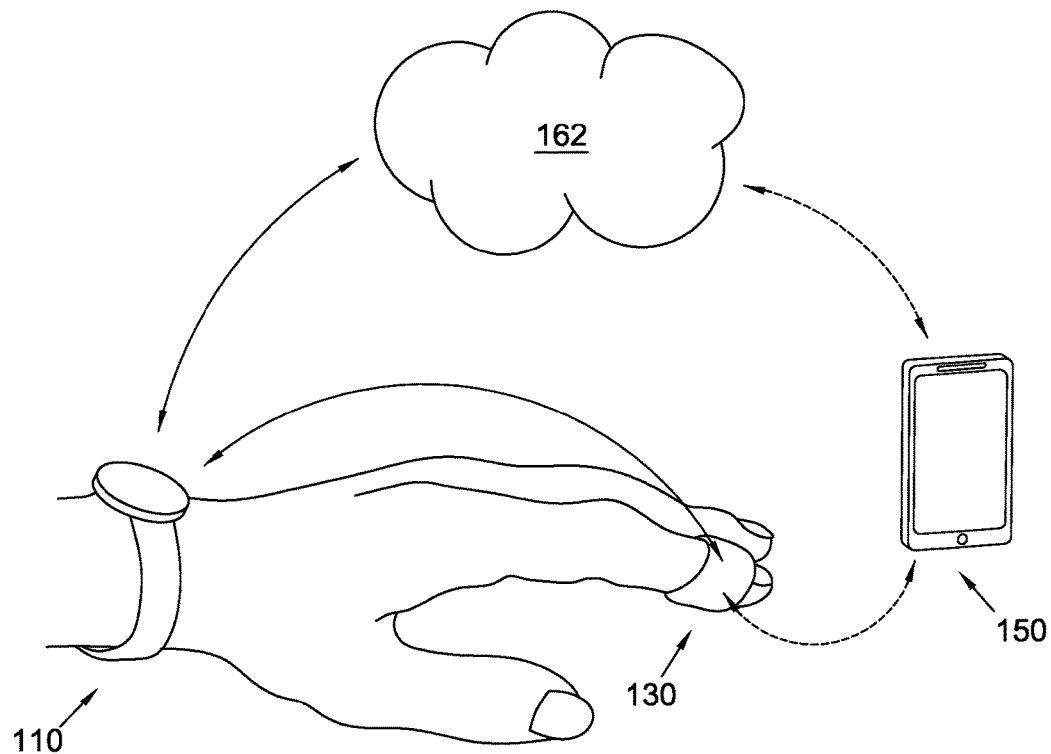
FIG. 3 shows an example wrist unit and fingerband for the system of FIG. 1.
Figure 4A:
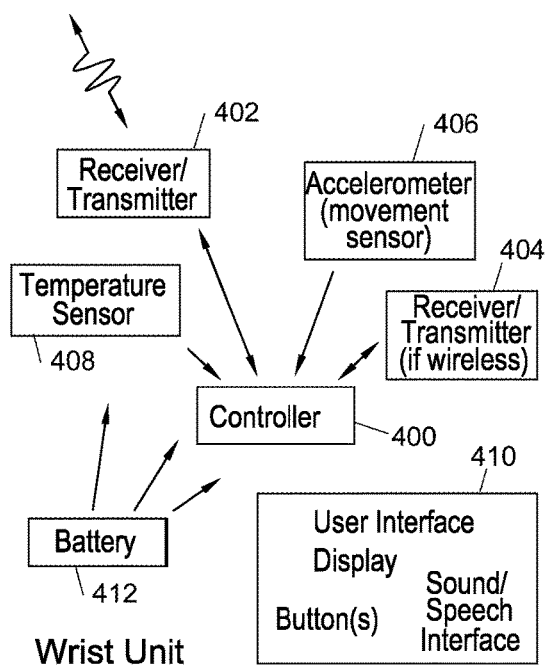
FIGS. 4a and 4b show block diagrams of the wrist unit and fingerband of FIG. 3, respectively.
Figure 4B:
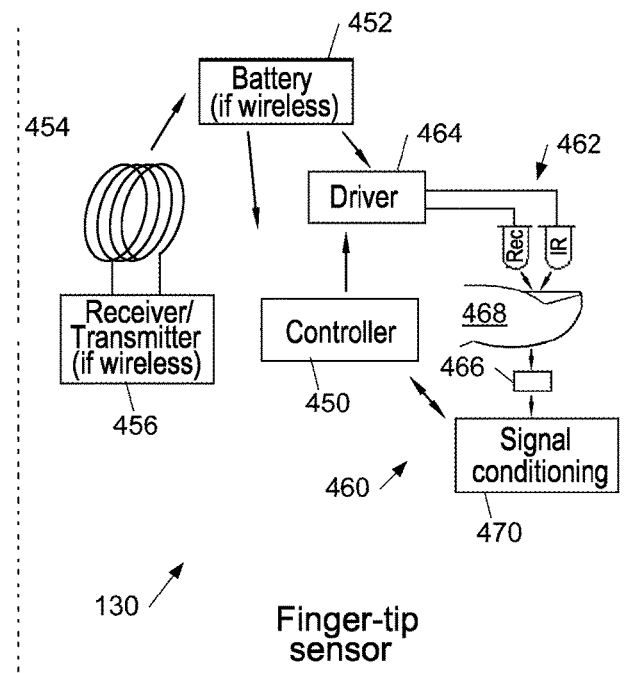

Referring now to FIG. 3, this shows an example physical embodiment of wrist unit 110 and fingerband 130. FIGS. 4a and 4b show more detailed block diagrams of each of these modules of the system. Thus, referring to FIG. 4a, a controller 400 is coupled to a first transmitter/receiver 402 to provide a wireless connection to a remote data processing system, in particular via the Internet and (where the connection to the fingerband 130 is wireless) to a second receiver/transmitter 404 for communicating with the fingerband. The wrist unit also includes an accelerometer 406 and optional temperature sensor 408 each also coupled to the controller. A user interface 410 is provided comprising for example, a display and one or more soft or physical buttons, and optionally a sound/speech interface. The wrist unit is powered by battery 412, which is preferably rechargeable.

The fingerband 130 comprises a controller 450 powered by a rechargeable battery 452 (in wireless embodiments) which is curved to fit the form factor of the fingerband shown in FIG. 3 and encapsulated within the fingerband. The batter is charged via an inductive loop 454 which in embodiments also serves as an antenna for a receiver/transmitter 456 which communicates with receiver/transmitter 404 of the wrist unit. The fingerband also includes a pulse oximeter sensor system 460 comprising one or more pairs of optical emitters typically light emitting diodes, operating at different wavelengths typically the red and infra-red, to provide a differential signal. These are driven by driver circuitry 464 so that when one is on the other is off, to alternately illuminate a sensor 466 through a user digit 468. The signal from sensor 466 is provided to signal conditioning circuitry 470 which, in embodiments, digitises an AC part of this signal, providing the digitised signal to controller 450.

Figure 5:
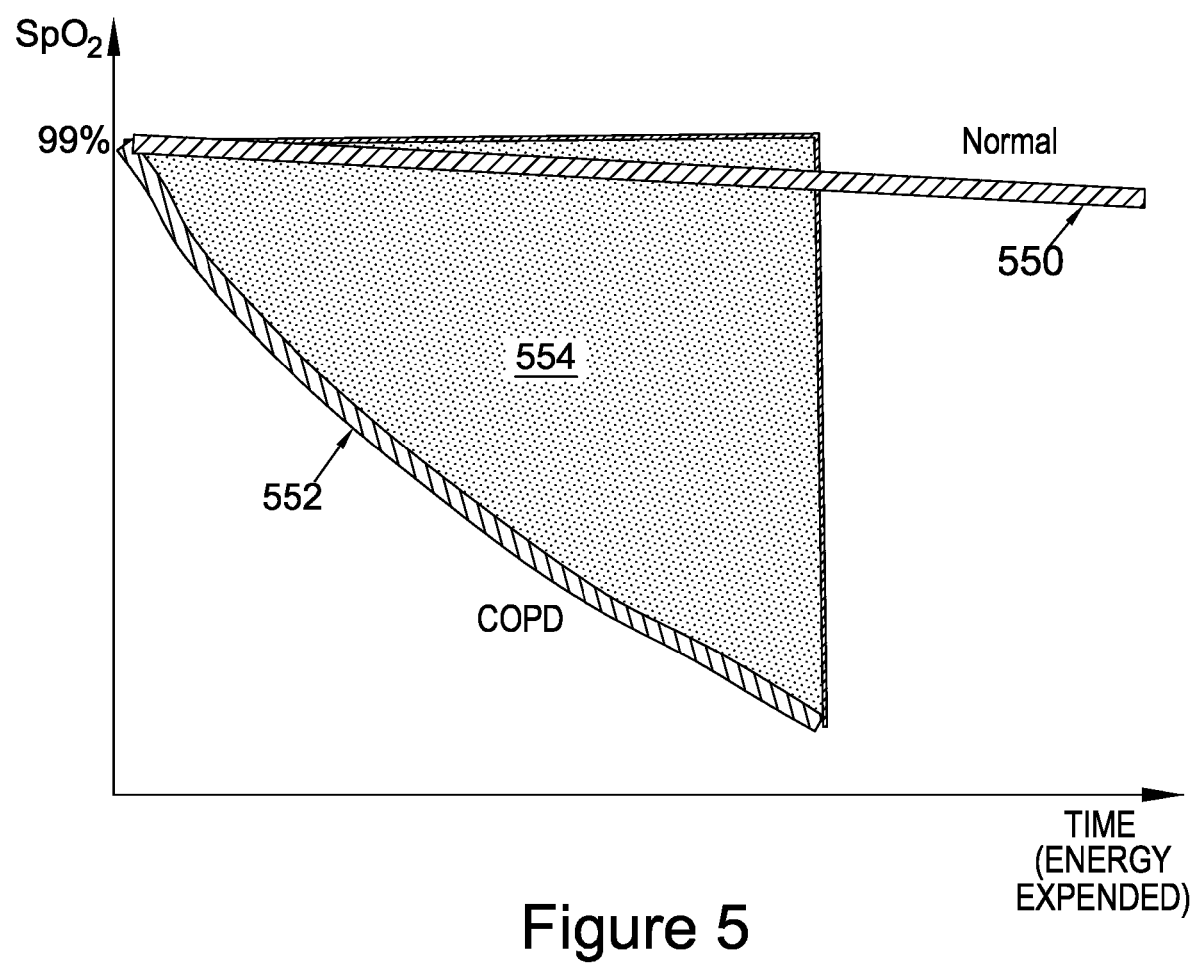
FIG. 5 shows an example of an $SpO_2$ curve during an exercise capacity test, illustrating, a technique for determining oxygen debt for use in embodiments of the invention.

Referring now to FIG. 5, this shows, schematically, a graph of $SpO_2$ oxygen saturation against energy expended (exercise duration) for a normal user 550 and a for a user with COPD 552. As can be seen, the oxygen saturation decreases substantially with time over the duration of the exercise and the desaturation area 554 (the integral of the oxygen desaturation) represents a measure of the cumulative oxygen debt of the subject. This may be combined with data representing the level of exertion to provide an exercise tolerance parameter, referred to herein after as a Respiratory Exercise Tolerance (RET) index. Embodiments of the invention can be used during daily life to track and report progression of disease, provide end of life forecasts, and alert in the case of respiratory distress, based upon this index. In broad terms the RET index combines one or more parameters relating to the degree of oxygen desaturation with one or more parameters relating to the level of physical effort exerted by the subject, preferably also taking into account the mass of the subject, to create a parameter representing the level of tolerance to exercise exhibited by the subject.

Embodiments of the system we describe may optionally provide further functions including, for example: communication with a remote computer for logging data, analysis, and alerts to assist management of subjects; sensing temperature to assist with the diagnosis of an infection; tracking whether or not medication is taken (for example using a camera); and the like.

It is important to measure both the level of induced oxygen desaturation and movement of the user during activities such as walking or sitting to standing, climbing stairs, and the like—activities that are typically used in the assessment of chronic lung disease. To achieve this, the sensor measuring oxygen saturation in blood (expressed as $SpO_2$) should be resistant to movement relative to the tissue being measured as such movement disrupts the signal. In embodiments, the most suitable arrangement was found to be a band on a finger which is able to communicate with the separate processing unit which also houses the accelerometer and means for communication.

In embodiments the RET index measures the energy expended by the wearer and correlates this with the measure of duration of and amplitude of desaturation. Preferably this compensates for the mass of the wearer. It also reduces the influence of the degree of motivation of the wearer when performing the test at any given time and thus the influence of the wearer's state of mind. In embodiments the Exercise Capacity Test may be the 6 minute walk test, the sit-to-stand test, the shuttle walk test or the TCasper test.

In the following f( ) denotes a mathematical function. Thus in one embodiment:

Respiratory Exercise Tolerance Index=$f_{RET}$(desaturation;energy expended)

In another embodiment:

Energy Expended by subject=$fe$(detected movement; body characteristic(s))

Then, for example:

Respiratory Exercise Tolerance Index=$fd$(desaturation):$fe$(energy expended)

For example:

Energy Expended by subject=$f$(distance moved by user and/or duration of exercise and/or average or total magnitude of motion;+optionally weight/BMI/other)

Or, if motion detection is not employed:

Energy Expended by subject=test-dependent constant×duration

In one embodiment:

$fd$(desaturation)=1/Desaturation Area

With this definition, a high value indicates a high level of tolerance to exercise.

Preferably the index also takes account of the weight of the subject and since energy expended in moving the subject's body depends on the subject's weight. Thus the RET index may include a component to allow for different weights of the participant as well as automated means for the measurement of oxygen desaturation and of the level of energy expended. Optionally data relating to the height of the subject may also be captured for a more accurate determination of energy expenditure from the accelerometer data (since the energy expended will in general depend upon height as well as weight).

In embodiments the measure of energy expenditure determined from the user motion (accelerometer) signal may be an absolute measure in the sense that it is a function of distance moved and one or more body characteristics; for example a measure of energy may be determined from a product of force (the upwards component of force is dependent upon weight) and distance. In other embodiments the measure of energy expenditure may be a relative measure (that is a value which is inherently dependent upon a body characteristic such as weight/height), for example a duration of movement/number of repetitions of a movement. Depending upon the measure of energy expenditure there may be both an absolute component and a relative component. In general the oxygen (de)saturation data, whether a measure of (de)saturation, or data derived from this such as a cumulative oxygen deficit value, is "relative" data in the sense that it relates to a concentration of oxygen in the blood rather than to an absolute, "volumetric" measure of the difference between oxygen intake and oxygen consumption. In embodiments, therefore, the height of the subject may be used to adjust one or both of the energy expenditure data and data derived from the (de)oxygen saturation signal so that the energy expenditure and an oxygen (de)saturation measure may be employed on an equal footing in determining the exercise tolerance parameter or RET index. For example, the height of the subject may be used as a measure of the subject's absolute or volumetric lung capacity, and thus this may be employed to scale or otherwise modify an oxygen (de)saturation measure to convert this to an absolute measure for combining with an absolute measure of energy expenditure from accelerometer data to determine the exercise tolerance parameter or RET index.

In one embodiment the system we describe supports the measurement of the common forms of Exercise Capacity test by instructing the user to perform a certain set of actions:
(1) It measures the physical movement of the subject during the test (eg number of steps in a 6MWT or repetitions in a STS test);
(2) It accounts for the weight of the subject;
(3) It measures $SpO_2$ before and during, for whatever time period the subject can endure;
(4) It combines these measurements to form an index to report the severity of cardiovascular and/or respiratory disease.

Using this approach, embodiments of invention are able to: (a) predict the risk of mortality within 24 months; (b) measure the effectiveness of interventions or medication; (c) alert to rapid rate of decline of the patient's capacity for exercise; (d) allow for variations in the level of effort invested by a given patient on different days; and (e) normalise between patients of differing weight. Further, these determinations can be undertaken during everyday life because the fingerband monitoring device is wearable and resistant to movement artefacts in its measurements.

Another aspect of embodiments of invention is that if measurements throughout daily life are not possible, at suitable intervals the wearer may be reminded to undertake a RET index test while wearing the device. This may be done using a "push" alert as a reminder, after which the device instructs the wearer what actions should be performed. This may be implemented in the form of a simple "wizard" on the screen of the device, with voice commands (with an in-built microphone and speaker) to guide the wearer through the process, telling them what to do and when to begin and finish.

This replicates verbal instructions from the technician, who now no longer needs to be present but may review the results remotely.

Thus some preferred embodiments of invention measure:
1. Level of effort exerted during an Exercise Capacity test. The integrated accelerometer counts acceleration events and their amplitude between the start and stop of the assessment used to provide desaturation (eg 6MWT or STS). Embodiments of invention are able to calculate the energy expended by the subject throughout the duration of the assessment. The subject's weight may be incorporated into the assessment by using this to scale a measure of the motion of the subject (eg amplitude and/or duration). Optionally the data may also be modified (eg by a scale factor and/or offset) dependent upon which, or which type of, exercise capacity test is used. In embodiments the type of Exercise Capacity tests may be selected by the wearer before initiating the test.

2. $SpO_2$ before and during the physical activity may be used to determine the total destaturation (desaturation×duration) ie the area under or over the curve (either could be used).

By combining parameters, which preferable include the subject's weight, embodiments of the system create a simple numerical index which can be used to inform the clinical team as to the rate of decline in prognosis or the severity of disease, for example compared with other subjects. This also allows patients to be risk-assessed in the community, for example to determine a level of care that will be needed.

Advantageously, embodiments of invention allow for variations in the patient's day-to-day motivation to perform the test. Embodiments of invention also provide the ability to compare of people of differing levels of obesity, so as to determine which patients are at the greatest risk. Such a comparison may be made more accurate by including age and/or gender and/or ethnicity. Embodiments of invention allow this process to be performed continuously in daily life rather than during irregular visits to a clinic or laboratory setting. Preferred embodiments of invention provide substantially continuous monitoring of the level of oxygenation during moderate physical activity.

Preferred embodiments of invention employ pulse oximetry, although embodiments of invention are not limited to using this technique. Pulse Oximetry is typically performed using two or more wavelengths of light, usually red and infrared, passed through the same tissue (usually the fingertip, but potentially forehead, earlobe, base of finger, foot and elsewhere), from which the amplitude of light variation due to the heartbeat is determined. The percentage of haemoglobin that is saturated with oxygen is calculated from the ratio of absorption at these two different wavelengths. This gives an approximation of the level of oxygenation of the arterial blood. Suitable implementations are well-known to those skilled in the art.

In pulse oximetry differential absorption signals can be lost with movement, because the arrangement of the emitting lights and sensors relative to the tissue is disturbed. To address this a statistical approach (averaging) may be employed but in preferred embodiments of invention we focus on the generation of a stable signal during exercise, through the design of a finger-worn $SpO_2$ monitor employing a relatively tight fingerband; this may be worn throughout the day and night. Thus we employ a $SpO_2$ sensor which fits closely to the finger and which, being lightweight, can tolerate low levels of movement during the 6MWT or STS (are patients who are ill do not move too vigorously).

Preferred embodiments of invention also warn the user should the Exercise Capacity test appear to be leading towards respiratory collapse, by alerting when $SpO_2$ falls below a threshold, for example 88%. In this case the test is terminated and the RET index calculated with the data available to that point.

Embodiments of invention also calculate the RET index intermittently throughout everyday life, and thus in a preferred embodiment the system comprises wearable monitoring device. Subject testing throughout the day is useful; operating intermittently (rather than continuously) helps to conserve battery power. The RET index can thus also provide a useful parameter for monitoring the beneficial effects of oxygen therapy and/or the positive or negative impact of medication.

Additionally intermittent measurements may be made, for example, once every 5-10 minutes while the subject is at rest to generate a baseline. The accelerometer in the wrist unit is used to instruct when to begin measuring when exercise has started. At that point SpO2 measurements may be taken substantially continuously until the exercise (movement) ceases. In embodiments rapid desaturation, even while at rest, triggers more frequent measurements, and ultimately an emergency alert mode if $SpO_2$ falls below 88% either while at rest or during a RET index determination.

It can be necessary to use the device to instruct the wearer to keep still if a successful test has not been obtained for longer than a threshold duration (eg 24 hours), for example because the wearer has been moving too much to acquire a good and stable signal or has not been moving sufficiently to create a desaturation event. Embodiments provide a "take a test" mode, during which the wearer is asked to keep still while a measurement is acquired (20 seconds) to confirm function. In a further mode the user is instructed to remain still whilst an initial SpO2 measurement is made, perform an exercise, and then remain still again whilst a final SpO2 measurement is made.

Preferred embodiments of invention embed the components of the fingerband pulse oximetry electronics, and some of the processing required, in a very small and close fitting silicone (more generally elastomer) finger (or thumb) band. This provides reduced sensitivity to disturbance due to movement because it fits snugly and is very lightweight. In embodiments the band is sized to fit the user's digit (a range of predefined sizes may be provided); this helps ensure the good fit needed for motion intolerance. Preferred implementations employ wireless communication to provide data to the (heavier) main processing unit and display (typically wrist-mounted), again to reduce movement artefacts.

In this way embodiments of the system provide an exercise tolerance measurement system, and a web-backend, in a form suitable for "until end of life" use. This is helpful in supporting patients with long-term respiratory conditions to self-manage.

Some example use cases are described below:

Supporting Pulmonary rehabilitation: this includes structured exercise programmes, but these are typically 3-12 weeks in duration. Behaviour changes are not retained after 3 weeks but greater changes are retained after 26 weeks of intervention—embedding motivation into daily life is essential. Tools are required to support patients and are much in demand. Embodiments of the invention may be used by phyisiotherapists to maintain adherence and then extend motivation into peer-to-peer communities such as Activ8rlives (on-line) and the British Lung Foundation's Breathe Easy project (group meetings) with remote monitoring of the data generated by our Invention by health coaches (physiotherapists, pharmacists or community nurses and so forth).

Self-monitoring: home-use technologies motivate adherence to oxygen therapy and medication. Physical activity and healthy eating, need long-term intervention initiated as part of a pulmonary rehabilitation programme. Embodiments of the invention may be used to continuously inform the wearer of their progress in meeting their health management goals.

Management of co-morbidities: COPD patients have more co-morbidities, around +3.7 additional health conditions; and COPD patients with lower physical activity have more co-morbidities. Regular physical activity by COPD patients improves cardiac function, body composition, well-being, insulin sensitivity and reduces blood pressure and inflammation. Active COPD patients have higher FEV scores and a slower decline in lung function. COPD patients with low levels of physical activity have a higher risk of mortality. are two different measures. Embodiments of the invention can be used both to track and to inform and support patients with multiple co-morbidities, in particular via physical exercise monitoring using the RET index.

Obesity: This is prevalent in 50% of COPD patients. Those who are overweight have a higher risk of recurrence of exacerbations. Weight management is an important part of maintaining health and embodiments of the invention can account for the differences in weight in tolerating exercise, providing useful feedback for the wearer about the impact of their weight.

Fingerband Sensors for Pulse Oximeter Systems

We now describe preferred embodiments of a fingerband and related pulse oximeter systems which may be employed with the above described techniques for measuring the exercise capacity or tolerance of a user. However embodiments of the fingerband we describe are not limited to use with such techniques and may be used with any pulse oximeter or related system, for example with a remote processing unit, such as a wrist unit, smartphone or smartwatch.

Broadly speaking we will describe a fingerband sensor in the form of a wide elastic band to be fitted around the end of the finger, but leaving the tip exposed to facilitate touch and handling of objects.

For optimum convenience and reliability under conditions of long-term wear, it is desirable to minimise the size and mass of the finger band. An effective arrangement is a combination of a fingertip band and another body-worn (e.g. wrist) additional unit that provides additional processing and communication. This may be a dedicated device or a smartphone or smartwatch; any of which can provide wide area communication, movement or temperature sensing, storage, processing or many other functions.

In embodiments short-range communication (e.g. Bluetooth) minimises the power required in and complexity of the fingertip band.

Form and Material of the Band

The band is moulded from soft high-grip rubber (around 20 to 40 Shore A) so that it conforms to the finger and holds in place with only moderate pressure. Many types of suitable rubber are available that are also suitable for low cost moulding processes. Good examples are silicone rubber and soft grades of thermoplastic elastomers (TPE). It is important that only moderate pressure is exerted by the band otherwise blood flow is reduced and it may also become uncomfortable.

Rubber encapsulation (overmoulding) of the sensing components conveniently provides environmental protection for durability; the internal components, with sufficient coverage by rubber, dictating the overall size of the band. However, this implies a certain overall thickness, typically around 2 or 3 mm, and a width of maybe 15 mm. A thinner and narrower section may be desirable to reduce the stiffness of the band so that it conforms better to the finger. Stiffness can be reduced by using softer grades of rubber, but they are more susceptible to tearing which is undesirable for durability. It is possible to make bands in a range of diameters so that an appropriate tension/pressure is achieved for a given finger. The fingerband should be a snug fit but not so tight as to restrict blood flow. In embodiments of the systems we describe, therefore, a set of fingerbands of different sizes (diameters) may be provided. A fully-customised band may be made to suit not only the size but also the shape of a particular finger, optimising fit and grip at minimum pressure. Preferably Long term wear of a band around the finger raises potential problems of compatibility with the skin, sweating and cleaning to remove dirt and prevent bacterial or fungal growth. These can be solved by choice of materials and design of the band. Features that can be helpful include:

Choice of the grade of rubber to avoid skin irritation

Figure 6A:
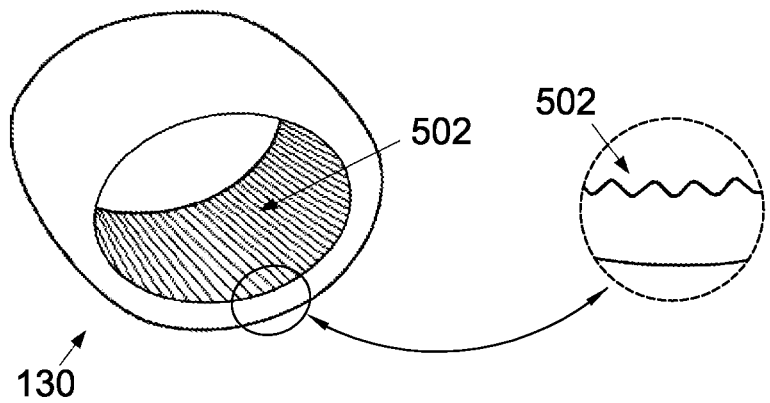
FIGS. 6a to 6d show, respectively alternative embodiments of a fingerband for the pulse oximeter system of FIG. 1, and a schematic illustration of an example pulse oximeter sensor.

Referring to FIG. 6a, grooves 502 along the inside of the band and/or perforations through the rubber, where these avoid the internal components, to allow "breathing" for sweat to evaporate. More generally a fingerband as described herein may incorporate one or more apertures in the band to allow the wearer to perspire, particularly when exercise is performed.

Figure 6B:
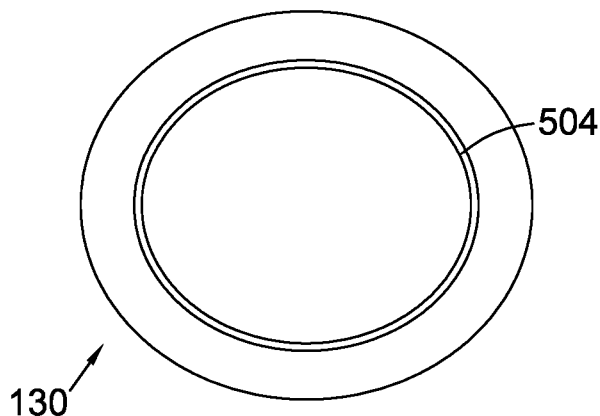

Referring to FIG. 6b, a layer of fibrous material 504 on the inside of the band, either coated onto the rubber of as a separate (possibly interchangeable or disposable) component. The material is chosen for wicking/breathing performance and for compatibility to the skin to avoid irritation.

Figure 6C:
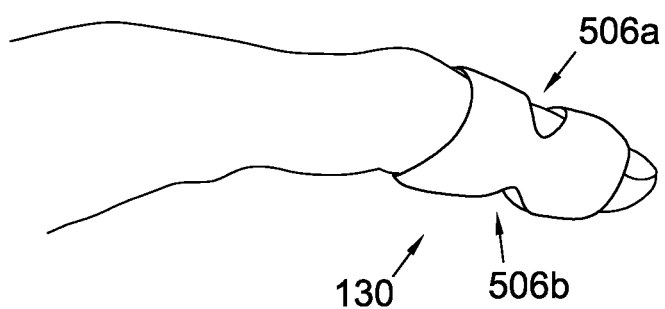

A challenge with current electronics and battery technology is accommodating the parts within a small band. The diameter of the band is dictated by the finger, which may be small for some individuals. The thickness of the band is limited by managing tension (as discussed previously) and convenience while wearing: to avoid bulk that would be awkward during daily tasks. The length of the band, along the finger, may be limited to a part of the terminal phalanx but this may not leave enough space for the parts, given the other restrictions. If this is the case an alternative is to extend the band onto the middle phalanx. However it is desirable to maintain flexibility of the joint between the phalanxes. Referring to FIG. 6c, a method to do this is to include a gap 506a,b in the band coinciding with the palmar (and/or the dorsal) faces of the finger respectively, connectivity remaining at either side.

Pulse Oximetry

Methods of measurement are well known to those skilled in the art and, most economically, use multiple LED light sources and one or very few silicon photodiode detectors. Independent measurements are taken using code, frequency or (preferably) time-division multiplexing of LED drive and detector signal processing. Sequential pulse drive to the LEDs is commonly employed, with the detection system sensing the difference in photodiode current between LED drive on and drive off states, for each of the LEDs. This provides some rejection of ambient light. Other modulation and detection schemes offer different balances of noise rejection, power consumption and complexity of processing. For a small finger band it is preferred to use a pulse or code-division modulation scheme and digital processing to extract the measurements for individual LED channels. This is to minimise the size of the electronics, particularly analogue, by using integrated digital processing circuits as far as possible. Since a high measurement rate is not necessary for the target uses (e.g. one measurement every few minutes or less frequently), it is possible/preferable to use a programmed microcontroller rather than dedicated logic for processing; the controller being used for other purposes (such as communication) between measurement activities.

Figure 6D:
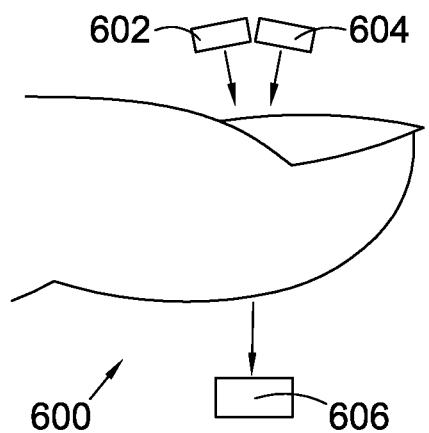

To obtain a satisfactory pulsatile signal for estimation of blood oxygen, it is desirable to illuminate/trans-illuminate a section of tissue which includes arteries. Anatomy of typical fingers has arteries running longitudinally along either side of the middle phalanx, dividing into a network in the tissue around the distal phalanx. This bone is relatively thin so that illumination on any side of the fingertip will pass through both the bone and surrounding tissue to the other side. It is, therefore, not critical how illumination is applied and sensed but it is important for pulse oximetry that it is stable. FIG. 6d shows, schematically, an example pulse oximeter sensor 600 comprising a pair of LED light sources 602, 604, typically one red, one IR; and a photodiode 606. Since the fingertip tends to be flattened across the palmar and dorsal faces, it is generally preferred to locate light emitters and sensors on these opposing faces, and it has been found that this also gives somewhat improved sensing performance.

Though it is possible to use most parts of the tissue surrounding the first phalanx for pulse oximetry, best sensing performance is typically obtained by using a path substantially through the centre (measured laterally and longitudinally between the tip and first joint) and running between the palmar and dorsal faces.

A particular objective in this application is to maximise sensing reliability during long-term wear. When such a band is worn for a long time, typically it is subject to vibration, flexure and movement relative to the finger (around the circumference and longitudinally). This results in both quick and slow movements of the band relative to the finger. Such movements will degrade the quality of measurement by pulse oximetry and should to be minimised. Several features are preferably included to optimise this:

- The band is made of elastic, high grip rubber to conform well to the shape of the finger, provide reliable contact pressure to the skin surface and give high contact friction
- Shape of the band is optimised (optionally with a range of sizes, or even customised) to maximise contact to the finger surface
- Minimise mass of the band so that the forces due to acceleration and gravity are minimised
- Minimise the thickness of the band to optimise flexibility during finger flexing and reduce movement (relative to the skin) when common activities are undertaken
- Provide means for sweat to be evaporated or removed from the contact areas, so that it does not lubricate the contact between the band and the skin It is inevitable that the band will stretch and change shape during wear, but the arrangement minimises movement of the embedded light emitters and detectors relative to the local skin and internal finger structures.

An additional consideration is removal and replacement of the band, which is desirable for comfort, cleaning and recharging. When a band is placed on the finger it is preferred that it is placed in a consistent position, both longitudinally and circumferentially, so that variations in the sensing light path are minimised. This can be aided by various optional features:

- Oval, or other non-round, sectional shape to give a cue to the preferred circumferential location. If the band is made to be significantly stiffer and flatter on one side then this will tend to locate onto the dorsal side of the finger, and may even migrate to this position even if the band is misplaced initially. For this reason it is preferred that any internal circuit boards are arranged with a larger board on this side of the finger.
- Visual cues such as external shape or markings, or difference of colour of the rubber to indicate which side is intended to be placed on the dorsal and/or palmar side
- Tapered internal shape to fit onto the tapering shape of the finger, but with a small additional taper to locate onto the reducing diameter of the finger near the finger joint
- If the band extends onto the middle phalanx, such tapering can apply to both parts of the band. Further, cuts/slots between the two sections give preferred fit around the first joint.

Despite these features, there may remain some mispositioning of the band relative to the preferred sensing axis, and slow relative movement during wear. Therefore it is preferable to have a sensing system that is tolerant of misalignment. In conventional pulse oximetry techniques it is possible to obtain a measure of quality of the pulsatile signals for the various emitter/detector pairs. E.g.:

- RMS of varying light amplitude relative to steady light received
- Peak or bounded RMS of the autocorrelation function of the varying signal
- RMS of the varying signal, band limited to around the current heart rate (this uses tracking of the varying heart rate, which can be updated from a valid measurement by updating to a spectral peak derived from a valid signal).

A fingerband can be provided with multiple emitter sets (where an emitter set includes individual emitters for each of the sensing wavelengths e.g, red and IR) and/or multiple photodetectors so that oximetry sensing can be performed along a number of different axes. A controller in the band may then measure along each of the axes to determine which axis gives the best result. This axis is then used for a period of time before another all-axes test is performed. Should the quality of measurement of the chosen axis fall significantly, this may trigger an early all-axes test. With this arrangement, the band can adapt to misalignment or movement—improving reliability during long term wear.

Electrical Power

This is used to operate the various functions:

Illumination by LEDs

Processing of the received oximetry signal

Communication between the fingertip band and the additional body-worn unit

Control and other processing

Space and mass are very restricted in the band, and a battery power source is normally the largest internal component. Note that the term "battery" is intended to include single cells as well as multiple cells, and of both primary and secondary types, as well as, for example, a high-capacity capacitor. Hence it is advantageous to minimise power consumption and one or more of several strategies may be used to achieve this:

- Activate the LEDs and signal processing only occasionally—when a new oximetry measurement is desired. Long term monitoring typically needs only occasional measurements, perhaps once per 10 minutes or less frequently.
- Avoid oximetry measurement when there is vigorous movement. Under such conditions it is desirable to acquire data over longer periods in order to extract a reliable measurement, requiring more energy. It is better to delay the measurement until movement subsides and this can be detected by integrating a movement sensor (e.g. accelerometer) in the band or in the additional unit, communication between the units then being used to trigger/inhibit measurement.

Use low power-consumption circuits and technologies

Store results in the band until a batch of results can be transmitted to the additional unit; avoiding the power overhead of frequent short transmissions.

Include one or more algorithm in the control system of the band to allow the band to operate autonomously for extended periods without needing communication with the additional unit (wrist unit). For example, an algorithm may adapt the oximetry sampling rate according to programmable parameters and the measured oxygen saturation, sampling more frequently if the saturation falls. Additionally or alternatively the communication rate with the additional unit may be adapted in a similar way.

Even with such strategies, there is a balance between size of the band and battery life. Since encapsulation is preferred, it is therefore preferred to integrate a rechargeable battery in the fingerband, for example a laminar or curved battery, preferably a lithium ion battery. A system to recharge the battery is then provided, preferably off the finger (especially where multiple bands are provided for to a given user).

One system for recharging exposes two or more contacts via holes in the encapsulation. A charging fixture may then make connection to provide charging power using resilient contacts in the fixture. Optionally the contacts may be magnetic, to facilitate connection to a charger. The contacts in the band should be compatible with the body-worn usage; preferably they are gold or gold plated to avoid corrosion and minimise skin reaction.

Figure 7A:
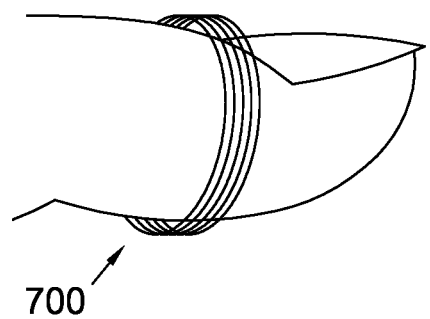
FIG. 7 illustrates induction charging coil configurations for a circumferentially wound coil, according to embodiments of the invention.
Figure 7B:
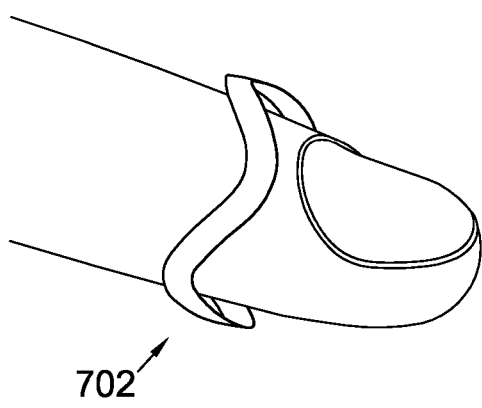
Figure 7C:
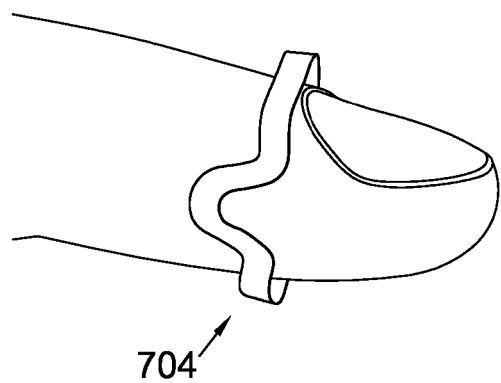

Alternatively the battery can be charged by induction via a coil built into the band. Such a coil may be wound either wound circumferentially ("around the finger") or tangentially. Both alignments are feasible, and both have pros and cons:

Tangential Alignment:
  Preferably need to align the coil in the band with a coil in a charging fixture. Since the band section is substantially round there is little inherent in the band to set the band in the correct alignment. Hence other mechanical features are preferably used to do this, or multiple coils (in a range of alignments) may be provided in the fixture
  The coil area is severely restricted and there is no opportunity to insert a ferromagnetic material into the coil of the band. This means relatively poor inductive coupling to a charging coil, therefore requiring high frequency operation and/or resonance which adds to the complexity and cost of the system Circumferential Alignment:
FIG. 7 illustrates some preferred configurations for a circumferentially wound coil 700 according to embodiments of the invention. Winding the coil around the circumference allows for large coil area, easy alignment and good coupling with a charging coil, and the option to use a ferromagnetic core to increase coupling. FIG. 7a illustrates a simple coil configuration. However, for efficiency and low cost it is desirable to use metal wire for the coil and the arrangement of FIG. 7a does not allow the degree of radial stretching that is desired. A solution to this is include a "meander" 702 or "joggle" 704 shape in the coil winding, as shown in FIGS. 7b and 7c respectively, thus making the coil compliant in overall diameter.

For manufacture, such a coil may be wound onto a former using an automated machine and may optionally be bonded to self-support without need for support (avoiding the extra space needed for a former). This is feasible at low cost so the better performance of the circumferential alignment makes this the preferred arrangement.

The battery, generally to be the largest component in the band, should be fitted into its curved shape. Batteries have conventionally been rigid and cylindrical or prismatic. Such batteries may be fitted into the band and multiple small batteries may be employed to maintain mechanical flexibility and provide sufficient capacity. However such an arrangement would be wasteful of space, because of the packaging of each battery/cell and space between them. Other types of battery are now available, in particular laminar-style lithium batteries of various formulations. Some of these can be flexed and curved, allowing better fit into the available space. This, in combination with their high energy density, makes them the preferred choice for battery type in the device.

Storage and Communications

Long term monitoring employs storage of, and access to, results and thus uses data storage and communications facilities. Since the size and mass of the fingertip band should be minimised, it is preferred to use the additional unit for some functions and remote computer system(s) for long term storage. This hierarchy minimises the size, mass and complexity of the body-worn devices and facilitates access (e.g. via Internet) to collated and processing of results.

All of the three elements (fingertip band, additional body-worn unit and remote computer system(s)) include storage of results, either long-term or short-term pending communication. Likewise, all include communication: Wide area (e.g. via Internet or Cellular data) between the remote computer and the additional unit and short-range (e.g. Bluetooth or LF inductive) between the additional unit and the fingertip band.

Various communication methods may be used between the fingertip band and the additional unit. To minimise the size, mass and power consumption of the fingertip band the preferred choices are presently Bluetooth LE or a custom LF inductive protocol (such as is commonly used for wireless chest-worn heart monitors) but other, more applicable, methods may be devised in the future. Either of Bluetooth or inductive can be small and low energy. The latter may use for communication the same coil as used for battery charging.

Control and Operating Modes

The device is optimally suited for long term monitoring of blood oxygen, and in this role the sensing and reporting may preferably be adjusted in response to conditions, both environmental and of the subject. Power consumption and battery life are linked; it is desirable that energy-consuming activities of the device are minimised so that the battery life is maximised. Basic sensing parameters are the rate at which new sensing measurements are taken, the rate at which they are reported and what other information is communicated. Various usage modes and behaviours are proposed:

Autonomous Fixed Rate:
  The device includes a setting to determine the time interval between successive measurements. Results can be reported at the same rate or at some other rate, using data storage in the device to hold results temporarily pending transmission Autonomous Variable Rate:
  Some algorithm in the device determines the rate of successive measurements. This may be on the basis of the measurement result, for example if the measurement shows low or falling saturation then it would be appropriate to increase the rate. Alternatively, local analysis of the measurement may detect poor quality, possibly due to movement, as shown by erratic changes or by low measure of quality of the pulsating absorbance signals. In such circumstances it may be appropriate to reduce the measurement rate, there being no benefit from making measurements that do not provide useful information and to save energy. When measurements show recovery of quality then the measurement rate can be increased to the normal rate. If a movement sensor is included in the fingertip device then high output from this may also be used to reduce the measurement rate or delay measurements until movement is sensed to have ceased or reduced.

Control Linked:

In all proposed configurations the results are communicated to another digital system, but it may also be advantageous for control information to be communicated to the fingertip device. This control information can be used to adjust the measurement rate or trigger/inhibit measurement or be used to manage data transfer. Various control schemes can be envisaged:

- Movement sensor in a separate, linked additional device detects when the subject is moving or not. The additional device sends control information to the fingertip device to slow or inhibit measurement when the subject is moving, and enables or increases speed of sensing when the subject is not moving, or is moving less.
- An algorithm in a separate, linked additional device or other digital system analyses the measured blood oxygen and/or other data to determine an appropriate measurement rate for the oxygen. This rate, or triggers is/are communicated to the fingertip sensor to determine the measurement times.
- A person (typically an expert), interacting with a linked digital system, reviews the condition of the subject and determines parameters to define the pattern of oxygen measurement. This may be simply a measurement rate (subjects at low risk could have lower rate of measurement, higher risk subjects having a higher rate) or may be a defined relationship between measurements and rate (e.g. if blood oxygen falls, the measurement rate is increased).

With two-way communication between the fingertip device and a linked digital system, the communications protocol can also include a transmission/acknowledge/retransmit-on-failure facility to improve reliability of communication.

Management of Measurement Data

Overall, the process comprises:
- Activation of the light sources
- Amplification, filtering and digitisation of the received photocurrent from the photodetectors
- Optional further filtering in the digital domain
- Extraction of the steady and pulsating (due to heart beat) amplitudes of the signals
- Calculation of the blood oxygen
- Analysis of the blood oxygen and triggering of consequent actions These steps typically include further processing, which may be those conventionally used for pulse oximetry. They may also include frequency band limiting and other techniques for rejection of noise and artefacts.

In preferred embodiments, processing is divided between the fingertip device and an additional linked digital system. It is important to choose which processing is done in the fingertip device so that all of the overall functions can be achieved while minimising the power consumption, complexity and data storage requirements of the fingertip device.

If the device is required to act autonomously on measured values then it is necessary to include sufficient processing to calculate those values. This employs more processing in the device than a configuration where the linked system determines the actions. However, in the latter case, two-way communications is used which implies increased complexity and power consumption. If very little processing is done in the device then more data is transmitted to be processed in the linked system. With minimum processing in the device, samples may be transmitted at 50 Hz or more to facilitate the linked system to be able to detect the pulsation amplitude reliably. However this high rate leads to increased power consumption for transmission.

It is therefore preferable to include sufficient processing in the device to reduce the data transmission requirement. Generally it is desirable to process data at relatively high rate up to the stage where the pulsation wave has been detected. Typically this uses knowledge of the heart rate, which varies, so some means of tracking the rate is employed. Various methods can be used, a simple one being to calculate the amplitude of the signal in a narrow band around a current value of heart rate; a high amplitude being indicative of accurate matching between the assumed and actual heart rates. This calculation can be repeated for rates above and/or below the current value; higher amplitudes indicating the assumed rate should be adjusted accordingly for a better match to the actual rate. Tracking of the heart rate can be done either in the device or in the linked system and communicated to the device. With a configuration such as this, much less data needs to be communicated to the linked system—such as amplitudes of pulsation waves, rather than high rate samples. Other configurations are possible and may be preferable, where processing is divided between the fingertip device and the linked system with the aim of achieving, for example, minimum overall power consumption (processing+communication) in the fingertip device.

Example

In one example fingerband, the AC component of red and infrared signals from a photodetector are digitised at a rate of not less than around 40-50 samples/second at, for example, 8-10 bits resolution. Data is captured for multiple heartbeats, for example 4-5 heartbeats, depending upon the degree of movement rejection desired. Thus data is captured for a time of 2-10 seconds or more, giving around 1000 samples (2000 if two sets of emitter-detector sensors). Depending upon the mode of operation this data may be captured substantially continuously or, for long-term monitoring, at intervals, of say 10 minutes. This data may be pre-processed to reduce the quantity of data prior to transmission, for example to determine peak-trough difference data for the pulsatile signal; and/or the data may be stored and transmitted in a batch, optionally at a reduced rate to save power.

Physical Configuration of the Fingertip Device

The desire for good fit to the finger and appropriate pressure onto the finger is explained previously, as is the concept of elastic material for the body of the device. However, within the device there are components that will not stretch and have no, or little, flexibility and these restrict the compliance of the overall device. Larger components cause more restriction, in particular the battery and circuit board(s). The sensing generally employs emitters on one side the fingertip and sensor(s) on the opposite side. It is convenient, but not essential, for sensors and emitters to be mounted on separate rigid circuit boards, rigidity being preferred to minimise mechanical stress on the components. Other electronic components (e.g. the processor and/or a Bluetooth module) may also be mounted on these circuit boards.

The connection(s) between the circuit board(s) may be flexible (e.g. if made as a "flex circuit"). Not only can it be flexible, it may also be made to be compliant longitudinally, for example using stretchable circuit board technology, in particular by including one or more (in-plane) convolutions, meanders or the like. Additionally or alternatively the connection(s) may comprise separately insulated fine wires (e.g. enamelled copper wire) for the interconnection, which also may include convolutions, meanders or the like to allow longitudinal stretch.

In preferred embodiments flexible batteries (e.g. "lithium polymer") are used; these are generally laminar in format. They can be shaped to wrap around the finger, but do not stretch. There are, therefore, two or three major components that do not exhibit longitudinal stretch: the circuit board(s) and the battery. It is preferred that these are located with the circuit board(s) on the palmar and dorsal sides of the finger with the battery wrapping around one side between, or overlapping, the circuit board(s). Thus in embodiments of the fingerband the battery, sensors and electronics may have a C-shaped configuration, around the circumference of the fingerband but open at one part of the circumference to allow the fingerband to stretch. This implies that only the side opposite to the battery offers significant stretch, but this is sufficient to provide compliance around the finger provided the band is sized appropriately to the finger.

Figure 8A:
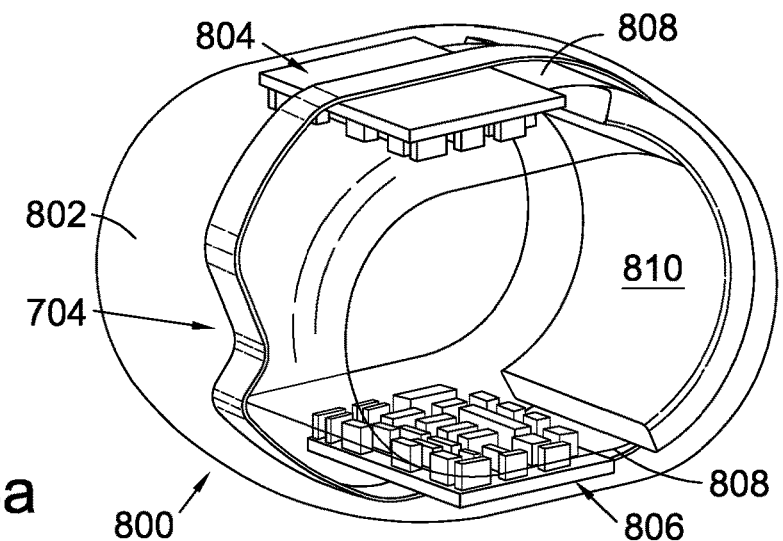
FIG. 8 shows design drawings illustrating the physical configuration of a fingerband according to an embodiment of the invention.
Figure 8B:
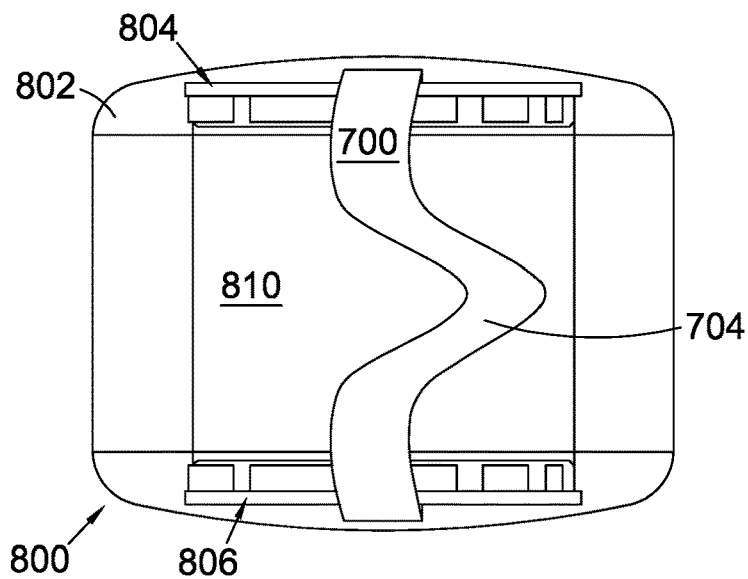
Figure 8C:
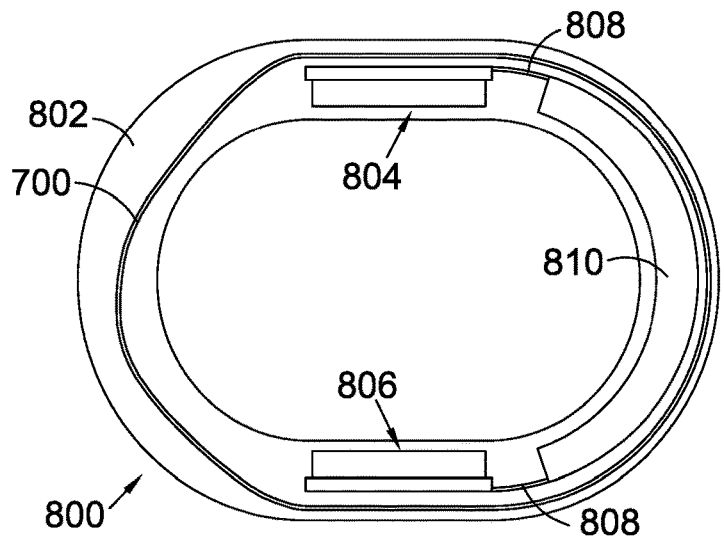

FIG. 8 shows design drawings illustrates the physical configuration of a fingerband 800 according to an embodiment of the invention. Thus FIG. 8a shows a perspective view of fingerband 800, FIG. 8b a view from the side, and FIG. 8c a view from the end, all showing the internal components embedded in the fingerband elastomer 802. Like elements to those previously described are illustrated by like reference numerals. In the illustrated example the fingerband electronics comprises a pair of circuit boards 804, 806, one carrying the light sources, the other the detector, connected via flexible connector (flexible circuit board) 808. (Alternatively all the electronics may be mounted on a single flexible and/or stretchable substrate). The fingerband is powered by a curved rechargeable battery 810.

Background Light

Using light (e.g. red and infrared) to measure blood oxygen saturation makes the system vulnerable to interference from ambient light around the fingertip band. Such effects can be addressed with opaque screens or shields around the finger and sensor. One can also make measurements of the increase of sensor output with the illumination operating (on) compared to the sensor output with the illumination cut off. However the inevitable time difference between the measurements results in a small remaining susceptibility. A high level of illumination (LED) also helps to reduce the effect of light interference by increasing the "wanted" signal in comparison to "noise". All of these techniques can be applied to the fingerband but the small size and restricted power consumption are particularly acute in this arrangement. Preferable embodiments use opaque elastomer for the body of the finger band, which greatly reduces ambient light reaching the sensor directly through the band, and also indirectly through the band and through the finger. Making the body of the fingerband itself opaque obviates the need for additional light-shielding components, but the emitters and sensors should then be embedded into the surface, avoiding covering the active areas with elastomer. This can be done by appropriate location of the devices into a mould before introducing the elastomer. Elastomers, such as silicone rubber, tend to be naturally transmissive of light but may be rendered substantially opaque by inclusion of dyes or particulates. It is desirable for the material to be substantially opaque both to red and infrared light and this can be difficult to achieve with single dyes. Multiple dyes or particulates selected for high absorption at both wavelengths (e.g. carbon black) are preferred for this purpose.

Charging Device

It is preferred for the battery in the fingertip band to be rechargeable so it is desirable to provide means to recharge the battery. Preferably this is done using one or more electrical contacts as previously described. Alternatively, however, electromagnetic induction to a receiving coil incorporated into the band may be used. The counterpart may then be one or more transmitting coils in a charging device, itself preferably powered from mains electricity but optionally from a second, higher capacity, battery.

Effective induction uses sufficient area of coil(s) and can be further improved by including ferromagnetic material (e.g. ferrite) to concentrate and couple the magnetic flux. The small size of the fingerband is a limitation of the size of the coil and this can be compensated by operating the induction at a high frequency e.g. 50 kHz~1 MHz or more. Use of resonance techniques also improves coupling between the charger and the band, but is more complex. Higher frequencies allow use of smaller coils but greater cost of the associated electronics and restriction of power due to radio frequency emission regulations. It is preferred, therefore, that the area of the receiving coil is maximised by winding it coaxial with the fingerband rather with its axis perpendicular to the axis of the band.

Any configuration of receiving coil should be substantially aligned relative to the axis of a transmitting coil. If the orientation between the band and a charging device is not known or controlled, there is the risk of inability to charge the battery in the band. In such circumstances an alternative is to provide multiple transmitting coils, preferably arranged so that one or more can be guaranteed to have suitable orientation to the receiving coil in the band. Either all coils can be energised, or a system can be included in the charging device to determine which transmitting coil has best orientation (judged by its electrical characteristics which are affected by orientation to the band and consequent energy transfer), then using only that coil to charge the band. Preferably, however, the receiving coil is coaxial with the fingerband and the charging device is provided with a mechanical feature in the form of a protrusion onto which the band can be placed to hold and orient it. The transmitting coil in the charging device is coaxial with the protrusion so that the two coils are arranged substantially coaxial. It is preferable that the protrusion also includes a ferromagnetic core to increase the coupling between the coils.

When the band is coupled with a charging device, power can be supplied not only to charge the battery in the band but also to operate circuits in it. In these circumstances, power consumption of the band is less critical so it is an opportunity to perform tasks that otherwise would cause undesired drain of the battery. In particular it is convenient to transmit data to the band and receive data from the band. This may be used for update of operating code or settings in the band or for download of measurement results. This mode is applicable when the band is on the charging device, and would not be used on the finger of the user. It would not operate in this way when being worn for active "live"

monitoring, however it may be a useful additional or alternative method to improve battery life for such monitoring.

Broadly speaking we have described a blood oxygen monitor comprising an elasticated tubular sensor including electro-optical emitters and sensor. The shape, material and internal structure of the sensor are suited for long term wear for monitoring. Power for the sensor is provided from an integrated battery which may be rechargeable from power received by a coil built into the sensor. The winding of the coil may be shaped to allow radial compliance of the tubular shape.

In embodiments the blood oxygen sensor comprises a substantially tubular elasticated body, at least one electro-optical detector, at least one pair of electro-optical emitters, a controller, a battery and a coil wherein the coil receives power to charge the battery and/or facilitates communication from or to the controller. Preferably the coil is oriented substantially coaxially with the tubular body and the path of the conductor in the windings of the coil includes deviations substantially from a circle coaxial with the tubular body. The blood oxygen sensor may have more than one pair of electro-optical emitters. In embodiments the blood oxygen sensor may further comprise a battery or cell of laminar format and substantially curved.

FingerBand SpO$_2$ Mechanical Design and Manufacture

In one embodiment 5 diameters of fingerband SpO$_2$ units are used so that a good fit of the band to the finger is obtained (too tight is uncomfortable and restricts blood flow while; too loose results in and poor measurements due to movement).

The integral battery within the finger band is charged using contacts exposed through the moulding. These and the sensors are held within a mould tool for injection of rubber around them (over-moulding). "Sacrificial" areas of the circuit board are provided to locate the components to the mould tool.

Figure 9A:
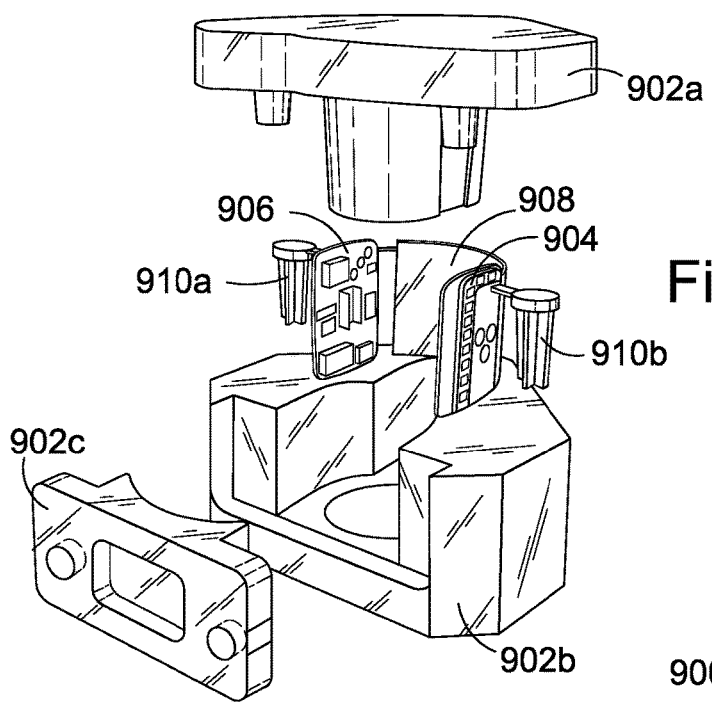

Referring to FIG. 9a, in one embodiment two PCBs 904, 906 are mounted on a flexible PC 908. The PCB assembly carries charging contacts 912 and/or an inductive charging loop, and preferably includes features to locate the battery.

Figure 9B:
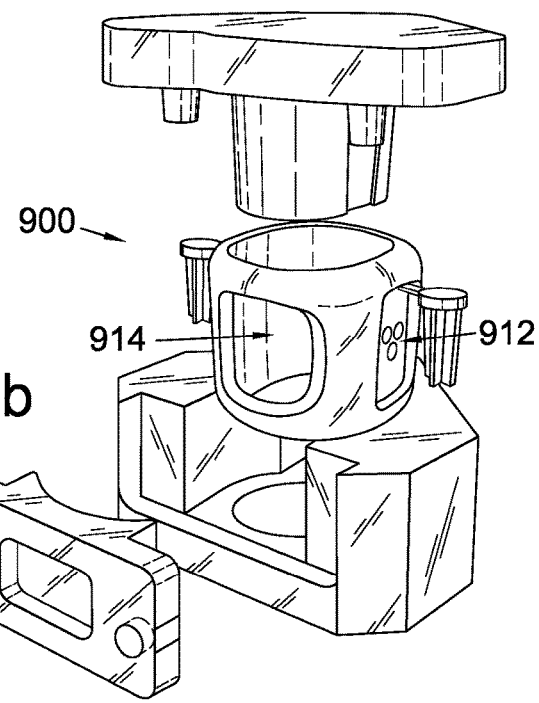

As illustrated, the assembly includes sacrificial parts 910a,b to locate the assembly in the mould tool 902a,b,c. When the over-moulding is completed (FIG. 9b), the fingerband unit 900 can be extracted from the tool and holding points removed. In the illustrated example the fingerband has exposed electrical contacts 912 to facilitate charging, and preferably holes 914 to allow the skin to breath and increase comfort during long-term wear.

Figure 9C:
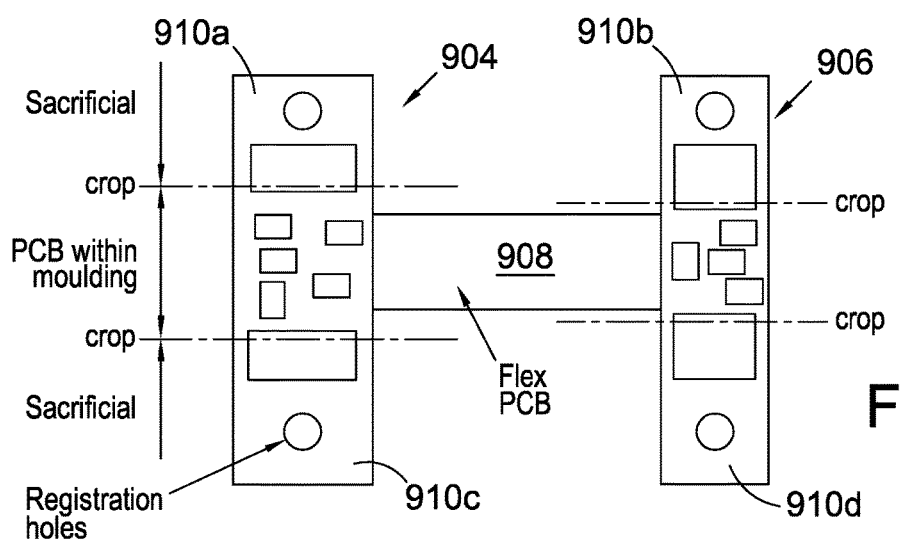

As shows in FIG. 9c additionally or alternatively PCBs 906, 906 may each include one or more sacrificial "wings" which extend beyond the region of the flexible PCB parts to locate the PCB assembly in the tool during over-moulding. These wings may afterwards be cropped.

Figure 10A:
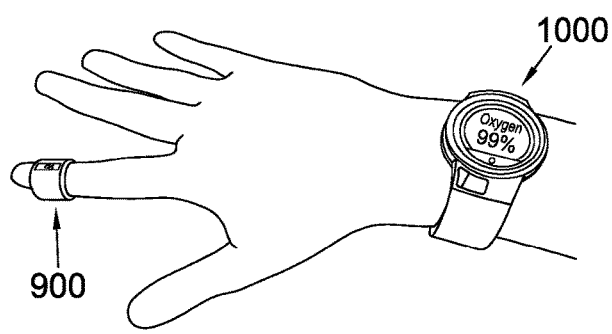
Figure 10B:
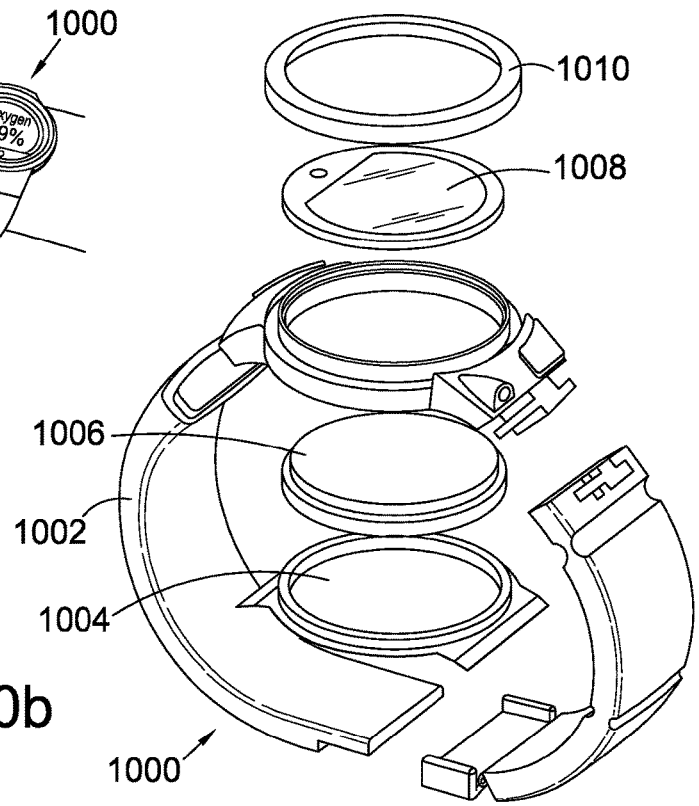

FIG. 10a shows the fingerband 900 in use with a wrist unit 1000 to display a levels of oxygenation of the user's blood (SpO$_2$). FIG. 10b shows an exploded view of the wrist unit comprising, in this example, a strap 1002, back 1004, PCB assembly (including a battery) 1006, display 1008 and optional bezel 1010.

Figure 10C:
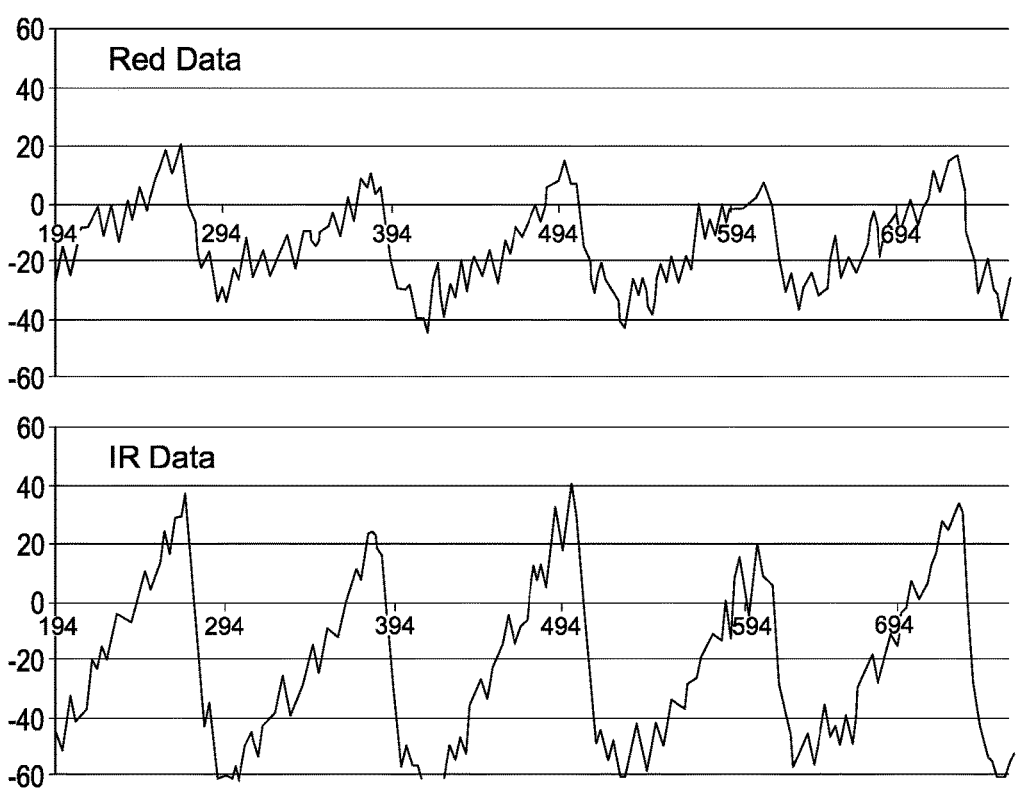

With this arrangement, a subject is able to wear the FingerBand SpO2 unit, walk briskly and transmit the data wirelessly to a receiving unit (on the wrist or elsewhere, or via the wrist unit), without substantial loss of or disruption to the signal. FIG. 10c shows example raw data from the two wavelengths of light passing through the finger of a user whilst walking briskly, captured after wireless transmission and unprocessed. The pulsation of the arterial vessels can be clearly distinguished from the total absorption of the tissues in the finger and the SpO2 can therefore be reliably derived even while the subject in motion. (In this particular example the measured heart rate was 57 beats per minute and the measured SpO2 was 97%, comparable to a traditional pulse oximeter value when the subject subsequently came to rest).

This approach represents a substantial improvement over existing approaches, and is particularly beneficial in determination of a Respiratory Exercise Tolerance index as previously described.

No doubt many other effective alternatives will occur to the skilled person. For example an ear (lobe)-mounted pulse oximeter sensor may be employed instead of a fingerband in aspects and embodiments of the invention.

It will be understood that the invention is not limited to the described embodiments and encompasses modifications apparent to those skilled in the art lying within the spirit and scope of the claims appended hereto.

The invention claimed is:

1. A user exercise-tolerance measuring pulse oximeter system, for determining the exercise tolerance or capacity of a user undergoing exercise, the system comprising:
   an elastic wireless fingerband comprising an optical sensor to provide an oxygen saturation signal, a chargeable power supply, and a wireless transmitter/receiver;
   a motion detector to provide a user motion signal; and
   a signal processor coupled to said wireless fingerband to process data from said optical sensor, and coupled to said motion detector;
   wherein said signal processor is configured to:
   process a combination of said oxygen saturation signal and said user motion signal to determine exercise tolerance data, wherein said exercise tolerance data is dependent upon said oxygen saturation signal and a level of exertion of said user determined from said user motion signal; and to
   time or count a period or quantity of user motion or movements, during said exercise, identified by said motion detector, to determine said level of exertion; to measure a degree of oxygen desaturation of blood of said user due to said exercise; and to output an exercise tolerance parameter;
   wherein said exercise tolerance data comprises said exercise tolerance parameter; and wherein said exercise tolerance parameter is a function of both said degree of desaturation and said level of exertion;
   wherein said processor is further configured to use said oxygen saturation signal to repeatedly measure a level of oxygen saturation during said exercise and to determine a derivative of said repeated measurements of said level of oxygen saturation with respect to time to determine an oxygen desaturation rate; and wherein said exercise tolerance data includes data representing one or more values of said derivative during said exercise such that said exercise tolerance parameter is dependent on said oxygen desaturation rate.

2. A pulse oximeter system as recited in claim 1 further comprising a user data input device, coupled to said signal processor, to receive user characterising data, wherein said user characterising data comprises one or more of: user weight, user height, user age, user gender, and user body mass index; and wherein said signal processor is configured to determine said level of exertion dependent on said user characterising data.

3. A pulse oximeter system as recited in claim 1 wherein said signal processor is configured to monitor said user motion signal over a duration of a period of user exercise, and to determine said level of exertion dependent on a cumulative measure of activity of said user over said period.

4. A pulse oximeter system as recited in claim 1 wherein said signal processor is configured to determine a prediction of a risk of illness or death of said user from said exercise tolerance data.

5. A pulse oximeter system as recited in claim 1, wherein said signal processor is configured to determine a measure of energy expenditure of said user from said user motion signal to determine said level of exertion.

6. A pulse oximeter system as recited in claim 1 wherein said signal processor is configured to determine a level of oxygen saturation for said user from said oxygen saturation signal, and wherein said exercise tolerance data is further determined dependent upon a difference between an initial level of oxygen saturation before said exercise and a final level of oxygen saturation immediately after said exercise.

7. A pulse oximeter system as recited in claim 1 wherein said processor is configured to use said oxygen saturation signal to repeatedly measure a level of oxygen desaturation during said exercise and to determine a cumulative oxygen debt of said user from the repeated measurements of said level of oxygen desaturation over a period of said exercise; and wherein said exercise tolerance data includes data representing a value of said cumulative oxygen debt.

8. A pulse oximeter system as recited in claim 1 comprising a wrist-mounting unit coupled to a fingerband, wherein said fingerband includes said optical sensor, wherein said wrist-mounting unit includes said signal processor and said motion detector, and wherein said motion detector comprises an accelerometer.

* * * * *